United States Patent
Lozecznik

(10) Patent No.: US 10,752,877 B2
(45) Date of Patent: Aug. 25, 2020

(54) FACULTATIVE ENDOPHYTIC PLANT GROWTH PROMOTING BACTERIA

(71) Applicant: Kontzamanis Graumann Smith MacMillan Inc., Winnipeg (CA)

(72) Inventor: Stan Lozecznik, Winnipeg (CA)

(*) Notice: Subject to any disclaimer, the term of this patent is extended or adjusted under 35 U.S.C. 154(b) by 146 days.

(21) Appl. No.: 16/008,404

(22) Filed: Jun. 14, 2018

(65) Prior Publication Data

US 2018/0371403 A1   Dec. 27, 2018

Related U.S. Application Data

(60) Provisional application No. 62/520,683, filed on Jun. 16, 2017.

(51) Int. Cl.
| | | |
|---|---|---|
| *C12N 1/20* | (2006.01) | |
| *C12R 1/38* | (2006.01) | |
| *C12N 11/14* | (2006.01) | |
| *C05F 11/08* | (2006.01) | |

(52) U.S. Cl.
CPC .................. *C12N 1/20* (2013.01); *C12R 1/38* (2013.01); *C05F 11/08* (2013.01); *C12N 11/14* (2013.01)

(58) Field of Classification Search
CPC ........................................................ C12N 1/20
See application file for complete search history.

(56) References Cited

FOREIGN PATENT DOCUMENTS

CA    3008344    12/2018

OTHER PUBLICATIONS

Valverde A et al., Differential effects of coinoculations with Pseudomonas jessenii PS06 (a phosphate-solubilizing bacterium) and Mesorhizobium ciceri C-2/2 strains on the growth and seed yield of chickpea under greenhouse and field conditions, Plant and Soil, Sep. 2006, vol. 287/1-2;43-50.

Oteino N et al., Plant growth promotion induced by phosphate solubilizing endophtic Pseudomonas isolates, Front. Microbiol, Jul. 22, 2015, vol. 6, Article 745, pp. 1-9 https://doi.org/10.3389/fmicb.2015.00745.

Parani K and Saha BK, Prospects of using phosphate solubilizing Pseudomonas as bio fertilizer, European Journal of Biological Sciences, 2012, vol. 4/2: 40-44.

Parnell JJ et al., From the lab to the frm: An industrial perspective of plant beneficial microorganisms, Front Plant Sci, Aug. 4, 2016, vol. 7, Article 1110, pp. 1-12, doi: 10.3389/fpls.2016.01110.

*Primary Examiner* — Bin Shen

(74) *Attorney, Agent, or Firm* — Michael R. Williams; Ryan W. Dupuis; Ade & Company Inc.

(57) ABSTRACT

Described herein are two bacterial strains, designated as KGS-2 and KGS-8 which have been shown to solubilize soil phosphorus and to enhance the growth of plants. In addition to promoting solubilisation of phosphate from sources such as dicalcium phosphate, manure and potassium phosphate, KGS-2 and KGS-8 also produce siderophore and indole-3-acetic acid (IAA).

15 Claims, 11 Drawing Sheets

Specification includes a Sequence Listing.

(* Indicate p-value< 0.05)

Note: 1=0 cells per seed, 2= $10^5$, 3=$10^6$, 4=$10^7$, 5= $10^8$, 6=$10^9$

SEQUENCE LISTING

<160> NUMBER OF SEQ ID NOS: 6

<210> SEQ ID NO 1
<211> LENGTH: 21
<212> TYPE: DNA
<213> ORGANISM: artificial
<220> FEATURE:
<223> OTHER INFORMATION: PCR primer

<400> SEQUENCE: 1
actttaagtt gggaggaagg g                                    21

<210> SEQ ID NO 2
<211> LENGTH: 21
<212> TYPE: DNA
<213> ORGANISM: artificial
<220> FEATURE:
<223> OTHER INFORMATION: PCR primer

<400> SEQUENCE: 2
acacaggaaa ttccaccacc c                                    21

<210> SEQ ID NO 3
<211> LENGTH: 21
<212> TYPE: DNA
<213> ORGANISM: artificial
<220> FEATURE:
<223> OTHER INFORMATION: PCR primer

<400> SEQUENCE: 3
acagaataag caccggctaa c                                    21

<210> SEQ ID NO 4
<211> LENGTH: 20
<212> TYPE: DNA
<213> ORGANISM: artificial
<220> FEATURE:
<223> OTHER INFORMATION: PCR primer

<400> SEQUENCE: 4
atctccgaag agatcggcct                                      20

<210> SEQ ID NO 5
<211> LENGTH: 20
<212> TYPE: DNA
<213> ORGANISM: artificial
<220> FEATURE:
<223> OTHER INFORMATION: PCT primer

<400> SEQUENCE: 5
acgcgggctt tcttctcttt                                      20

<210> SEQ ID NO 6
<211> LENGTH: 29
<212> TYPE: DNA
<213> ORGANISM: artificial
<220> FEATURE:
<223> OTHER INFORMATION: PCR primer

<400> SEQUENCE: 6
gttgcagtga tcaaggttgg cgctggttc                            29

FACULTATIVE ENDOPHYTIC PLANT GROWTH PROMOTING BACTERIA

PRIOR APPLICATION INFORMATION

The instant application claims the benefit of U.S. Provisional Patent Application 62/520,683, filed Jun. 16, 2017 and entitled "Phosphate Solubilizing Bacteria", the entire contents of which are incorporated herein by reference.

BACKGROUND OF THE INVENTION

Carbon, hydrogen, oxygen, nitrogen, phosphorus and sulphur are the primary elements essential to all life. Soils contain all of these elements in addition to other macronutrients and micronutrients which are needed for plant growth. Typically, such elements are not present in the soil in sufficient quantity or in forms that can support maximum plant growth and yield. In order to overcome these deficiencies, fertilizers having specific chemical constituents in specific amounts are often added to the soil, thereby enriching the growth medium. The fertilizers may be supplemented with certain trace elements such as copper, iron, manganese, zinc, cobalt, molybdenum, and boron, as oxides or salts containing the elements in the cationic form.

Agriculturally, metal ions are essential nutrients for plant growth. Soil deficiency because of the unavailability or exhaustion of metal ions is very often the cause of poor plant growth.

In the past, applications of phosphorus have typically been only about 20 percent efficient (that is, only 20 percent of the applied phosphorus is available to the crop in the year of treatment).

Phosphorus is routinely used in starter fertilizers applications. However, most phosphorus is immobile in the soil and subsequently small seedling roots have difficulty obtaining the necessary amounts for rapid growth. For these reasons, phosphorus is routinely used as a starter fertilizer, even when overall phosphorus levels in a field may be adequate or high. However, phosphate in the soil can interact with other nutrients and/or metals and immobilize them. Furthermore, there are obvious environmental concerns regarding high soil phosphate levels leaching into the environment as well as potential toxicity to seeds and plants.

Clearly, methods for reducing the amount of phosphorus applied as fertilizer as well as methods for more effectively and/or efficiently enabling plants to use phosphorus already in the soil are needed.

Plant growth promoting bacteria (PGPB) benefit commercial crops by improving both yields and plant tolerance to stresses (high salinity, drought, etc.). Some PGPB possess other beneficial traits such as bioremediation of hydrocarbon and heavy-metal contaminated soils (Cheng et al. 2007, Albano et al. 2016, Aukema et al. 2014). PGPB can interact with several economically important field crops including canola, soybean, wheat, and corn (Nehra et al. 2015). PGPB can promote higher crop yields and expedited or early crop emergence as well as growth under both stressed and optimal plant conditions (Cheng et al. 2007). This can occur from a variety of mechanisms including nutrient cross-feeding, modulation of plant stress hormones, and assistance in the creation of a beneficial rhizosphere environment to increase nutrient bioavailability (Nehra et al. 2015).

One important group of PGPB, *Pseudomonas* spp., have been found to modulate the plant stress response in order to improve the plant's tolerance to salinity, petroleum hydrocarbons, and heavy-metal toxicity (Cheng et al. 2007, Greenberg et al. 2007, Albano et al. 2016).

Of the *Pseudomonas* strains that have been described in the literature, multiple PGP features have been well-characterized at the physiological and molecular levels.

Typically three pathways strongly associated with PGP phenotype in *Pseudomonas* spp. are: i) IAA (indole-3-acetic acid) biosynthesis by PGPB from tryptophan secreted into the rhizosphere by the plant, uptake of IAA by the plant stimulates growth (Cheng et al. 2007); ii) 1-aminocyclopropane-1-carboxylate (ACC) degradation by the PGPB via an ACC deaminase, high levels of ACC cause a plant to elicit an ethylene production response that causes necrosis of the plant tissue (Cheng et al. 2007); and iii) catabolism of phenyl acetate as a growth substrate that is secreted from the plant into the rhizosphere to promote the growth of specific organisms (Basha et al. 2006). Phenyl acetate can also be consumed from inside the plant by specific bacteria, as such, its catabolism by bacteria can be linked to an endophytic lifestyle (Basha et al. 2006). Endophytic organisms can provide several benefits to the plants including modulation of plant hormones, increasing bioavailability of nutrients, and acting as a biocontrol agent (Parnell et al. 2016).

Typically, PGPB are also capable of solubilizing various forms of insoluble phosphate found in soils. For example, insoluble calcium phosphate by conversion of glucose excreted from the root of the plant to gluconate in the rhizosphere drives down the pH and increases the solubility, and therefore the bioavailability of phosphate near or on the plant roots (Buch et al. 2008). These organisms may also assist in making other forms of phosphate more bioavailable such as phosphate bound to organic material, phosphate bound to metals in the soil, and other forms of fertilizer phosphate such as struvite (Rodriguez et al. 1999). In doing so, PGPB have the potential to increase the availability of phosphate to plants. In most systems this could lead to a reduction of applied phosphate leading to reduced costs and increased yields to grain farmers in general.

SUMMARY OF THE INVENTION

According to an aspect of the invention, there is provided a biologically pure culture of KGS-2.

According to a further aspect of the invention, there is provided a method of increasing plant growth comprising: inoculating an effective amount of KGS-2 into a soil environment; and growing a plant in said soil environment, wherein said plant has increased plant growth compared to a plant of similar type grown in soil in the absence of KGS-2.

According to another aspect of the invention, there is provided a biologically pure culture of plant growth promoting bacteria KGS-2 *Pseudomonas jessenii* strain deposited as IDAC: 220318-01.

According to a still further aspect of the invention, there is provided a method for promoting or increasing or improving plant growth and/or plant yield comprising: preparing a composition comprising a high-density aliquot of plant growth promoting bacteria (PGPB) KGS-2 *Pseudomonas jessenii* strain deposited as IDAC:220318-01; applying said composition to a soil environment in which seeds or seedlings have been or will be planted; growing said seeds or seedlings into plants in said soil environment, said PGPB KGS-2 colonizing said soil environment and promoting growth of the plant; and harvesting said plants.

According to yet another aspect of the invention, there is provided a method for promoting or increasing or improving plant growth and/or plant yield comprising: preparing a composition comprising a high-density aliquot of plant growth promoting bacteria (PGPB) KGS-2 *Pseudomonas jessenii* strain deposited as IDAC:220318-01; applying said composition to seeds or seedlings that have been or will be planted, said KGS-2 penetrating said seeds or seedlings and establishing an endophytic relationship; growing said seeds or seedlings into plants in said soil environment; and harvesting said plants.

DESCRIPTION OF THE PREFERRED EMBODIMENTS

Figure 1:
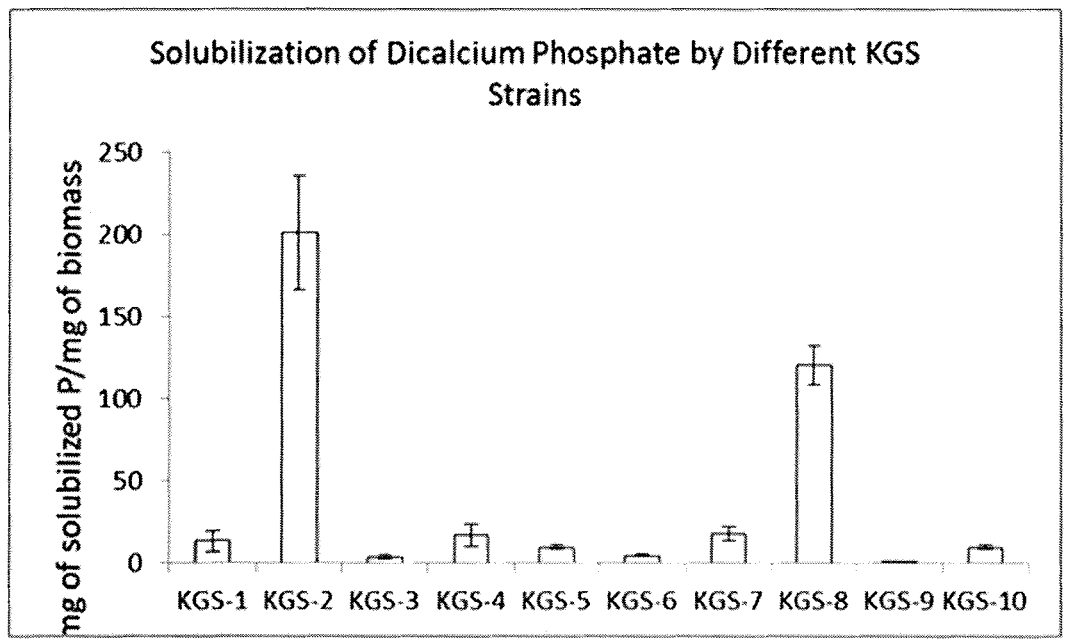
FIG. 1 is a bar graph showing solubilisation of dicalcium phosphate by different KGS strains.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "biologically pure" refers to a culture wherein virtually all of the cells present are of the selected strain.

As used herein, "inoculating" refers to introducing at least one bacterium into or onto a medium, for example, a liquid medium, granular product, carrier, peat powder, seed or a soil environment. For example, the bacterium may be coated on a seed or may be applied directly to the soil, as discussed herein As used herein, "soil environment" refers to the soil in which a plant is grown or is growing.

As used herein, "KGS-2" refers to a *Pseudomonas* spp strain, for example, a *Pseudomonas jessenii* strain, for example, *Pseudomonas jessenii* KGS-2, deposited with the International Depository Authority of Canada, National Microbiology Laboratory, Public Health Agency of Canada, 1015 Arlington Street, Winnipeg, Manitoba, Canada, R3E 3R2 under deposit number IDAC: 220318-01 on Mar. 22, 2018.

Described herein are two bacterial strains, designated as KGS-2 and KGS-8 which have been shown to solubilize soil phosphorus and to enhance the growth of plants.

Within this work, KGS-2's ability to interact with several commercial crops is shown, including spring wheat, winter wheat, canola, soybean, barley, fava and corn. KGS-2 has the ability to enhance wheat yields between 8.5%-13%, as discussed below. KGS-2 also appeared to alleviate the plants requirement for phosphate, showing an increased effect on yield in spring wheat with low phosphate. Several of the results demonstrate the ability of KGS-2 to modulate plant development at various stages of growth: i) early wheat and canola root and vegetative size; ii) the flowering window of canola; and iii) the number of tillers in wheat.

As part of the characterization of KGS-2 the genome was sequenced. From this information, it was found that KGS-2 is related to, but distinct from, UW4, a studied plant promoting organism. UW4 is distinct both on the basis of genome sequence and physiological properties, as discussed herein. Strain KGS-2 possessed genes linked to a lifestyle consistent with a bacterium living inside of plant tissue (endophyte); follow up experiments confirmed this, as discussed below. Based on the genes present within the genome, close interaction of KGS-2 and plants has benefits that would directly and indirectly increase yields such as modulating the growth hormone auxin and increasing disease resistance.

This is not surprising as endophytes live within a plant without causing disease but while also preventing other pathogenic or parasitic organisms from colonizing the host plant. In some cases, the endophytic organism penetrate the embryo with the host plant's seeds.

In almost every case where KGS-2 was found to interact positively with plants (canola, winter wheat, spring wheat, barley, soybean), germinating plant top and root length showed consistent increases in the early stages of growth in laboratory experiments. The most profound change was with spring wheat which doubled its total root length in germination experiments. As will be apparent to one of skill in the art, larger plants are indirectly linked to increased yields; as such, based on increased plant size during early growth, a yield enhancement is a sound prediction. The other crucial factor that greatly affects yield is stage timing, in particular when and how long flowering occurs. Flowers are highly sensitive to plant stressors such as drought or heat. Loss of flowers will directly decrease yields. KGS-2, and many PGP bacteria, decrease stress in the plant by modulating the plant hormone auxin. Plant stress directly affects plant maturity so therefore the plant flowering window; the flowering window can both be altered in time and duration.

Laboratory experiments included the measurement of the dosage of bacteria needed to observe a PGP effect at germination (>1000 bacteria per seed for wheat, >100 bacteria per seed for canola), as well as the development of methods for growing cells to very high concentrations (>$10^{10}$ cells per mL) and in larger quantities, indicating that growth of KGS-2 can be scaled up for commercial purposes.

According to an aspect of the invention, there is provided a method for promoting or increasing or improving plant growth and/or plant yield comprising:

preparing a composition comprising a high-density aliquot of plant growth promoting bacteria (PGPB) KGS-2 *Pseudomonas jessenii* strain deposited as IDAC:220318-01;

applying said composition to a soil environment in which seeds or seedlings have been or will be planted;

growing said seeds or seedlings into plants in said soil environment, said PGPB KGS-2 colonizing said soil environment and promoting growth of the plant; and harvesting said plants.

According to another aspect of the invention, there is provided a method for promoting or increasing or improving plant growth and/or plant yield comprising:

preparing a composition comprising a high-density aliquot of plant growth promoting bacteria (PGPB) KGS-2 *Pseudomonas jessenii* strain deposited as IDAC:220318-01;

applying said composition to a soil environment in which seeds or seedlings have been or will be planted;

growing said seeds or seedlings into plants in said soil environment, said PGPB KGS-2 colonizing said soil environment and promoting growth of the plants such that said plants shows increased growth compared to similar plants grown in an untreated soil environment; and harvesting said plants.

The composition may be applied to the soil environment as a liquid or may be applied to the environment as a powder.

As discussed herein, KGS-2 has been shown to increase growth in a wide variety of plants, including but by no means limited to spring wheat, winter wheat, canola, soybean, barley, fava and corn. Accordingly, it is maintained that KGS-2 is capable of improving growth in any suitable plant, as discussed herein.

It is of note that as discussed above, the improved or increased growth may be demonstrated by comparison with one or more plants of similar variety or breed grown under similar conditions except for the presence of KGS-2, that is, in an untreated soil environment. It is of note that this control does not necessarily need to be repeated every time.

As discussed herein, KGS-2 will increase or improve growth of a plant by for example increasing root growth, increasing shoot growth, improving or increasing plant tolerance to stresses such as soil salinity, drought, and hydrocarbon and/or heavy-metal toxicity, increasing soil phosphate bioavailability, increasing plant size during early growth, inhibiting fungal infection of the plant and by establishing an endophytic relationship with the plants.

For example, KGS-2 can increase plant growth by converting glucose to gluconate, thereby lowering local soil pH and enhancing bioavailability of phosphate present in the soil environment.

KGS-2 can also improve plant growth by producing mannitol-2 dehydrogenase, thereby inhibiting fungal infections.

KGS-2 can also improve or increase plant growth by synthesizing indole-3-acetic acid.

KGS-2 can also improve or increase plant growth by degrading 1-aminocyclopropane-1-carboxylate.

KGS-2 can also improve or increase plant growth by modulating levels of auxin.

KGS-2 can also improve or increase growth by penetrating stems of a plant or embryo of a seed, thereby establishing an endophytic relationship.

According to an aspect of the invention, there is provided a method for promoting or increasing or improving plant growth and/or plant yield comprising:

preparing a composition comprising a high-density aliquot of plant growth promoting bacteria (PGPB) KGS-2 *Pseudomonas jessenii* strain deposited as IDAC:220318-01;

applying said composition to seeds or seedlings that have been or will be planted, said KGS-2 penetrating said seeds or seedlings and establishing an endophytic relationship;

growing said seeds or seedlings into plants in said soil environment; and harvesting said plants.

According to an aspect of the invention, there is provided a method for promoting or increasing or improving plant growth and/or plant yield comprising:

preparing a composition comprising a high-density aliquot of plant growth promoting bacteria (PGPB) KGS-2 *Pseudomonas jessenii* strain deposited as IDAC:220318-01;

applying said composition to seeds that will be planted, said KGS-2 penetrating said seeds and establishing an endophytic relationship;

growing said seeds into plants in said soil environment; and harvesting said plants.

The composition may be applied to the seeds as a dry powder or may be applied to the seeds as a liquid.

As such, a high-density aliquot of a specific bacterial strain of *P. jessenii* (KGS-2) is used for promoting plant growth.

As will be appreciated by one of skill in the art, the high-density aliquot refers to what is essentially an effective amount of KGS-2 for promoting or improving or increasing growth of a plant. As discussed herein, an effective amount will depend on several factors, including the type and/or variety of the plant, the type of soil and in particular the concentration and type of nutrients present in the soil, and the growth conditions expected to be encountered by the plants during their life cycle.

Accordingly, as used herein, a high-density aliquot refers to an aliquot that has at least $10^3$ colony forming units per ml or at least $10^4$ colony forming units per ml, or at least $10^5$ colony forming units per ml or at least $10^6$ colony forming units per ml or at least $10^7$ colony forming units per ml or at least $10^8$ colony forming units per ml or at least $10^9$ colony forming units per ml or at least $10^{10}$ colony forming units per ml. In some preferred embodiments, a high-density aliquot is at least $10^5$ colony forming units per ml or at least $10^6$ colony forming units per ml.

Figure 19:
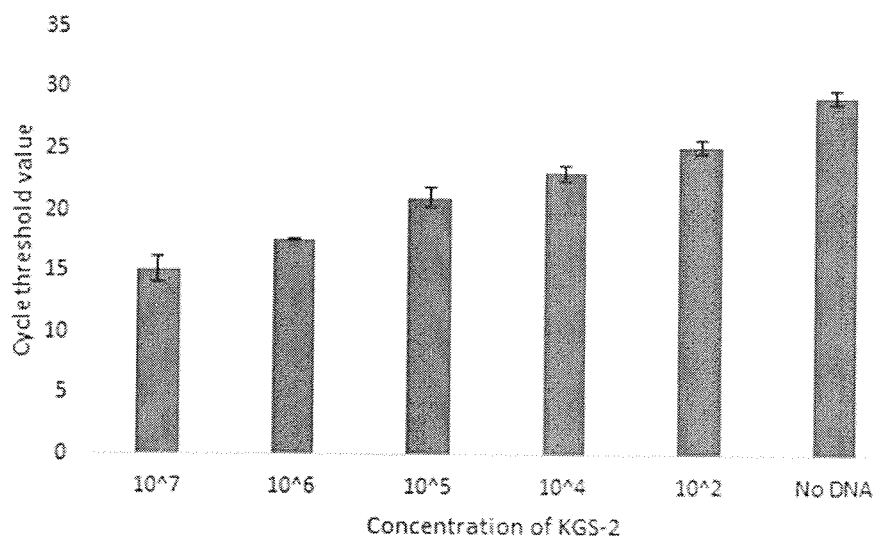
FIG. 19 shows bacterial levels in soil.
Figure 20:
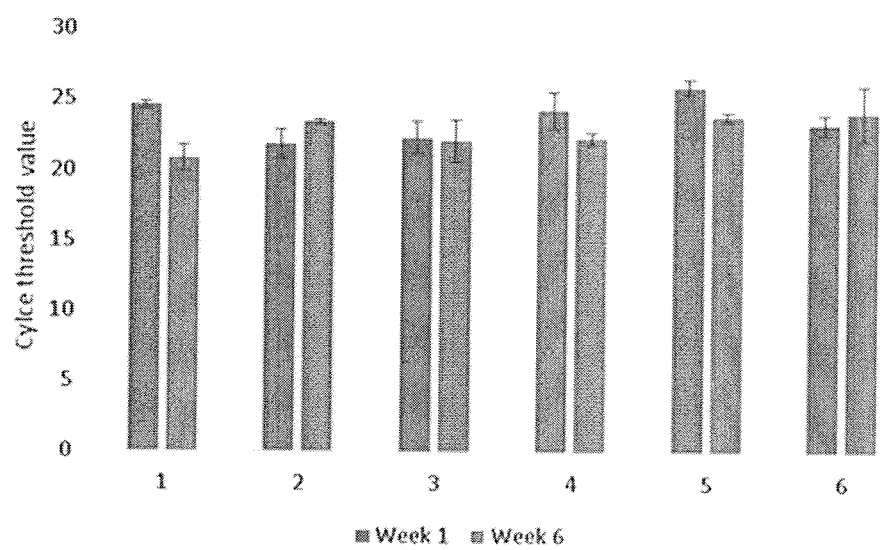
FIG. 20 shows change in bacterial levels in soil over time.

Specifically, administration of a high-density aliquot of the bacteria is essential for the establishment of a culture that can colonize the rhizosphere of the growing plant and/or establish an endophytic relationship with the plant. This is necessary for survival of the bacteria in the soil environment because of the presence of competitors and predators, as discussed below and as shown in FIGS. 19 and 20.

Specifically, in its natural environment, KGS-2 is beset by predators and competitors, making it impossible for the establishment of a culture of sufficient density to convey beneficial effects on plants growing within the soil environment. Specifically, KGS-2 must not only compete with other bacteria for nutrients, the bacteria are also beset by protozoa, worms, arthropods and bacteriophage which will eat or infect/lyse the bacteria, thereby significantly reducing numbers of the bacteria and/or limiting the ability of the bacteria to establish within the soil.

Only by increasing the number of bacteria at "any given location" is the strain able to outcompete other bacteria already present in the soil for nutrients and survive the attack of predators present in the soil to exist at a density sufficient for plant growth to be promoted by KGS-2, for example, by increasing bioavailability of phosphate in the soil, by synthesizing IAA, by degrading ACC, by modulating auxin and by establishing an endophytic relationship with the plant.

As such, it is maintained that at least one of the biological functions or physical properties of a high-density aliquot of KGS-2 has been changed as compared to the corresponding bacteria occurring in the wild as a result of the physical condition of the bacteria being present at a sufficiently high culture density. Specifically, as discussed above, at a sufficient density, the bacteria are able to promote growth of the plant. However, in the wild, the presence of predators and competitors makes it impossible for KGS-2 to establish itself at a sufficient culture density for these benefits to take place. However, administering a high-density aliquot to the soil results in the establishment of a colony of KGS-2 that has different biological function (promotion of plant growth), different biological activity (lowering of soil pH by conversion of glucose to gluconate; modulating auxin levels; synthesizing sufficient IAA to promote plant growth; degrading sufficient ACC to prevent tissue necrosis) and physical properties (high-density of colony) than what occurs in the wild. Furthermore, applying a high-density aliquot either immediately prior to or immediately after planting in the soil or applying a high-density aliquot to a seed or seedling prior to planting allows for KGS-2 to penetrate the stems of the seedlings or the seeds, thereby establishing an endophytic relationship which as discussed herein has numerous benefits for plant growth.

In liquid form, the cells to be used as inoculant were viable for greater than 4 weeks.

The growing season in which KGS-2 (2017) was applied was highly adverse to the crops planted, regardless of the use of a plant growth promoting bacteria. Despite these adverse conditions there was a clear increase in yield. KGS-2 applied to wheat yielded an 8.5%-16% increase. Canola decreased in yield consistent with the midsummer heatwave, disproportionally affecting the flowering period. While a decrease in yield may seem to be a negative, it did show that KGS-2 interacts strongly with canola. Furthermore, the early growth measurements of canola showed that they had more yield potential. Application of KGS-2 directly at the time of seeding in canola will likely help realize the increase in yield potential, as discussed herein.

Accordingly, in some embodiments of the invention, a high-density aliquot of KGS-2 is applied to the soil either immediately prior to planting, simultaneously with planting, or immediately after planting.

The application of this high-density aliquot can be done as liquid suspension or as solid materials applied to soil, potting mixture, seeds, seed pieces, seedlings, foliage, carrier materials, roots and planting soil. For example, KGS-2 may be coated onto a seed or seed piece, may be applied as a powder, may be applied as a liquid, may be applied foliar or as a suspension to a soil environment or may be mixed into a soil environment prior to use of the soil environment for planting. As discussed herein, KGS-2 is a facultative endophyte that will also increase and/or improve plant growth by solubilizing phosphate, synthesizing IAA and/or by degrading ACC.

In some embodiments of the invention, the high-density aliquot may be administered to the soil as a liquid or a powder, for example at a density of at least $10^3$, $10^4$, $10^5$, $10^6$, $10^7$, $10^8$, $10^9$ or $10^{10}$ colony forming units per ml.

In other embodiments, the high-density aliquot may be applied to a carrier and then applied to the soil for example but not necessarily as a powder. As discussed herein, the carrier may be is a seed wherein KGS-2 is coated onto the seed. In some embodiments, the seed may be coated with peat or clay or mineral or vermiculite or polymer prior to application of a high-density liquid aliquot. Alternatively, a carrier such as peat, clay, diatomaceous earth, a mineral, vermiculite, perlite granule, a polymer or the like may be mixed with a high-density liquid aliquot and then dried, as discussed herein. The dried carrier comprising the high-density aliquot may then be applied to the seed or to the soil, as discussed herein.

Alternatively, the carrier may be a liquid suspension, for example, an agriculturally compatible oil.

The clear positive effects of KGS-2 on wheat yield can be seen in other wheat yield components such as: i) the number of tillers, wheat stems that may result in an extra wheat head, increased by 30% in KGS-2 treated wheat; and ii) number of wheat heads increased ~10% in KGS-2 treated wheat. Furthermore, the dose response of KGS-2 treatment on wheat was linear indicating the response has not been saturated. Yield improvements measured for the KGS-2 inoculated wheat, nevertheless, were between 8.5% and 13% and could possibly be increased even further by using a more effective inoculation formula applied directly to the seed.

Several members of the genus *Pseudomonas* such as *Pseudomonas aeruginosa*, *P. putida*, and *P. fluorescens* are shown as endophytes (grow inside the plant) with the ability to enhance plant growth (Andreote et al. 2017, Devi et al. 2017, Lally et al. 2009). In this study, the ability of KGS-2 cells to enter into the plants and exist as endophytes in canola, wheat, and corn is shown. We were able to recover live cells of KGS-2 from the stems of both wheat and canola at harvest time, demonstrating that they persisted in the plant environment for the entire growing season, but also confirming their capacity to act as endophytic PGP bacteria.

As discussed herein, in addition to promoting solubilisation of phosphate from sources such as for example but by no means limited to dicalcium phosphate and manure, for example, hog manure, KGS-2 also produces siderophore and indole-3-acetic acid (IAA).

Specifically, genomic analysis indicates that KGS-2 comprises several metabolic functions that are linked to the plant growth promotion including but not limited to: i) the ability to degrade the plant stress causing agent ACC (using 1-aminocyclopropane-1-carboxylate deaminase); ii) the ability to synthesis IAA from tryptophan; and iii) the ability to catabolize phenyl acetic acid.

As will be apparent to those of skill in the art, the phenyl acetic acid degradation pathway also plays a role in the degradation of aromatic compounds for bioremediation, meaning that KGS-2 can be used to promote plant growth while also removing undesirable aromatic compounds from the soil environment.

As will be appreciated by one of skill in the art, the promotion of plant growth by KGS-2 may involve multiple effects in addition to the P solubilization, such as for example but by no means limited to iron binding and plant-hormone production. Of course, the specific characteristics of KGS-2 promoting plant growth in a specific instance will depend on many factors, including but by no means limited to soil type, soil pH, types of nutrients present/absent in the soil and amount thereof, environmental conditions such as temperature, moisture, and humidity and the type of plant grown in the soil environment.

As discussed herein, KGS-2 promotes greater root and shoot length and also improves seed vigour.

Specifically, the International Seed Testing Association adopted the definition of seed vigour as "the sum total of those properties of the seed which determine the level of activity and performance of the seed or seed lot during germination and seedling emergence". The formula can be expressed as:

Vigour index=(shoot length+root length)×germination rate

The application of KGS-2 for promoting plant growth can be done as liquid suspension or as solid materials, which can then be applied to soil, potting mixture, seeds, seed pieces, seedlings, foliage, carrier materials, or planting soil.

For example, KGS-2 may be coated as a liquid or a powder onto a seed or seed piece. Thus, when the coated seed or seedling is planted in a suitable soil environment, KGS-2 will colonize the area immediately surrounding the seed or seedling, thereby solubilizing phosphate by lowering the local pH by converting glucose to gluconate in the soil, either already present or applied as a fertilizer, as well as providing other plant growth promoting activities such as for example but by no means limited to degrading ACC, synthesizing IAA, modulating auxin levels and catabolizing aromatic compounds present in the soil. As will be appreciated by one of skill in the art, these growth-promoting activities take place whether or not an endophytic relationship is established.

Alternatively, KGS-2 may be applied as a powder, for example, onto either a seed or a carrier material. These strains may also be applied as a powder to a soil environment or may be supplied in a powdered form for application to soil environment, as discussed herein.

Alternatively, KGS-2 may be applied as a liquid, for example for foliar application or as a suspension that is applied to a soil environment, for example, to the surface of the soil environment, or may be mixed into a soil environment prior to use of the soil environment for planting.

In another aspect of the invention, there is provided a biologically pure culture of KGS-2.

It is of note that other *Pseudomonas jessenii* strains which are closely related to, but biologically distinct from KGS-2, have been demonstrated to: increase growth in rice fertilized with cow dung extract, increase growth and heavy metal uptake in *Ricinus communis* grown in soil contaminated with heavy metals; and inhibit growth of *Phytium aphanidermatum*, phytopathogen that causes damping off and root and crown rot disease in cucumber. Other strains of *Pseudomonas jessenii* have been reported to have properties that favour plant growth promotion (Rajkumar et al., 2008).

Strain KGS-2 can be distinguished from all other strains available in the public databases of bacteria genes on the bases of the full sequences of its 16S rDNA sequences which have been designated and identified below.

KGS-2 has seven 16S rDNA sequence:
Gene ID: 2713981717, locus tag: BOO88_00715
Gene ID: 2713982373, locus tag: BOO88_03995
Gene ID: 2713982684, locus tag: BOO88_05550
Gene ID: 2713985426, locus tag: BOO88_19260
Gene ID: 2713985852, locus tag: BOO88_21390
Gene ID: 2713986474, locus tag: BOO88_24500
Gene ID: 2713986771, locus tag: BOO88_25990

One particular *Pseudomonas jessenii* organism highly related to, yet distinct from the KGS-2 strain, is strain UW4, whose genome has also been sequenced. Extensive testing has been done on UW4 using stressors such as heavy-metal contamination, salinity, aromatic compound degradation, and plant growth promotion (Cheng et al. 2007, Albano et al. 2016, Aukema et al. 2014). KGS-2, while closely related to UW4, has unique physiology and distinctive plant interaction pathways when compared to UW4.

The KGS-2 genome is given in has 6,263,601 total bases and approximately 5,588 genes. Of particular relevance is that KGS-2 circular genome is completely sequenced. There is no genetic information missing, so the presence or absences of key genes can be stated confidently.

Figure 13:
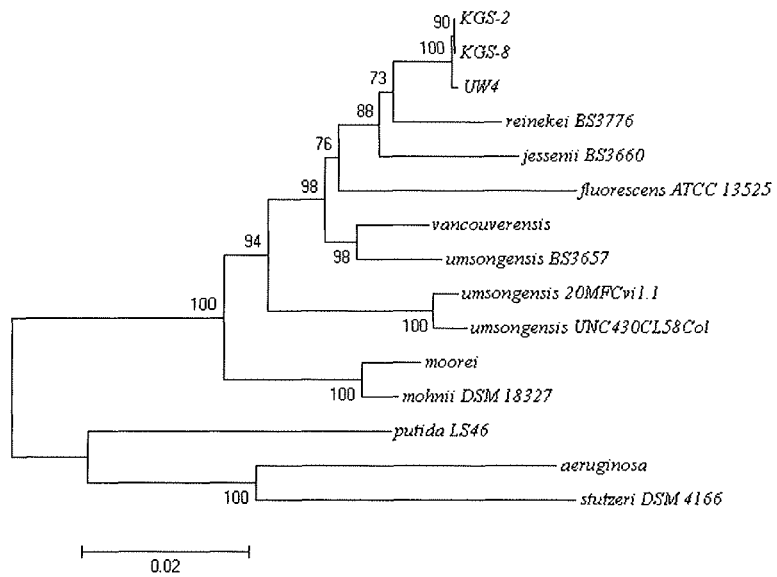
FIG. 13 is a phylogenetic tree showing the relatedness of plant growth promoting bacteria in the *jessenii* subgroup of the genus *Pseudomonas*.

Using the genome information, a phylogenetic tree was built using conserved genes, in order to determine the relatedness to other organisms. The cpn60 gene was used due to its good resolution at the species and strain level (Verbeke et al. 2011). FIG. 13 shows the relatedness of plant growth promoting bacteria in the *jessenii* subgroup of the genus *Pseudomonas*. Based on this tree, KGS-2 is highly related yet distinct from UW4.

Due to its unique regions in KGS-2 relative to UW4, some differences in functions were predicted. For example, KGS-2 contains an operon for phenyl acetic acid catabolism that UW4 does not contain. Phenyl acetic acid catabolism is linked to an endophytic or pathogenic lifestyle due to its role in helping bacteria survive when internal to plant tissue by acting as a carbon source (Taghavi et al 2009). Of important note is the fact that UW4 has not been reported as an endophytic organism, but rather as a root associated organism. This means that the manner in which UW4 and KGS-2 interact with plants is quite different.

UW4 and KGS-2 have differences in the gene compliment for gluconate production from glucose. The production of gluconate can drive down local pH and enhance the bioavailability of phosphate for the plant and as such this may relate to differences in propensity to drive down the pH.

KGS-2, unlike UW4, does not have any annotated genes involved in phenazine synthesis (Jain et al. 2016), which can be used by *Pseudomonas* to inhibit the growth of other bacteria. On the other hand, mannitol-2 dehydrogenase, which can have a role in inhibiting fungal infection, is present in KGS-2 but not UW4, indicating that KGS-2 can have an effect on fungal infections (Patel et al. 2016).

In another aspect of the invention, there is provided a method of increasing plant growth comprising: inoculating an effective amount of KGS-2 into a soil environment; and growing a plant in said soil environment, wherein said plant has increased plant growth compared to a plant of similar type grown in soil in the absence of KGS-2.

As used herein, "increased plant growth" refers to any improvement in plant growth, including but by no means limited to a plant demonstrating more roots, longer roots, a more complex root architecture, more shoots, more stems, faster emergence, taller plants, greater yield per plant, greater biomass, higher quality plant product, plants that are more resistant or resilient to weather, disease or pests, and healthier plants, compared to plants grown in the absence of the plant-growth promoting bacteria.

In the Examples discussed below, for example, each canola seed was inoculated (the same day it was planted) with approximately $10^8$-$10^9$ cells of KGS-2 or KGS-8 per seed. As will be appreciated by one of skill in the art, KGS-2 and KGS-8 must be applied at a high enough concentration in the field to allow for the strains to compete with other indigenous strains naturally present in the soil. This can be done by a variety of means, for example by concentrating the cells for inoculation or double inoculation (using 2 different inoculation methods at the same time, for example, using both granular inoculant on seed and liquid inoculant on field rows).

As such, in some embodiments of the invention, a culture of KGS-2 is grown to a suitable density, for example, $10^5$ to $10^9$ cells per ml, prior to application to the soil environment or to a suitable carrier, such as a seed or substantially inert carrier material such as clay or peat or the like as discussed herein. As will be appreciated by one of skill in the art, applying KGS-2 to the soil at such a culture density is necessary to enable the bacteria to establish in and colonize the rhizosphere which is critical for the bacteria to beneficially affect plant growth within the rhizosphere.

As will be apparent to one of skill in the art, this may be accomplished by a variety of means. Furthermore, certain growth conditions may be used to promote or "emphasize" certain characteristics of KGS-2.

As discussed herein, both strains have been demonstrated to produce siderophore (iron chelating molecules) and indole-3-acetic acid (IAA), which are involved in plant growth promotion, as discussed herein and is of course well known to one of skill in the art.

Specifically, siderophores improve iron uptake by plants. In addition, the ability to produce siderophores is involved in the suppression of pathogens in soil. Siderophore-producing bacteria also have the ability to enhance phytoextraction of heavy metals from contaminated environments. (Beneduzi et al. 2012; Saha et al. 2013).

As discussed below, greenhouse data shows that the KGS-2 and KGS-8 promote growth in canola and corn. As such, it is a sound prediction that both strains will be able to promote growth of a wide variety of plants, as discussed herein.

The invention will now be further elucidated and illustrated by way of examples; however, the invention is not necessarily limited to the examples.

Example 1—Bacterial Isolation

Bacterial strains KGS-2 and KGS-8 were isolated from fields in Southeastern Manitoba.

Different serial dilutions of soil samples (in sterile water) were spread plated onto standard Pikovskayas (PVK) agar media to obtain single colonies. PVK contain 0.2% weight/volume of insoluble phosphate. For this experiment, dicalcium phosphate (DCP) was used as the source of insoluble phosphate. Colonies that formed a zone of clearance were purified 3 times before being stored at −80° C.

Example 2—Bacterial Solubilisation of Insoluble Phosphate Compounds

Strains were shown to be able to solubilize DCP and struvite. PVK media containing either DCP or struvite were utilized (0.2% weight/volume of either DCP or PVK was used). The bacteria were grown in 37° C. for 2 days (struvite), and 4 days (dicalcium phosphate). Ten strains showed some solubilisation capacity. Specifically, as can be seen in FIG. 1, KGS-2 (approximately 200 mg of solubilized dicalcium phosphate per mg of bacteria) and KGS-8 (approximately 125 mg of solubilized dicalcium phosphate per mg of bacteria) showed the greatest amount of solubilization and were selected for further study.

Example 3—Production of Plant-Growth Promoting Compounds

In silico analysis showed that that KGS-2 and KGS-8 possess the genes involved in 1-Aminocyclopropane-1-carboxylic acid (ACC) degradation, gluconic acid production, and siderophore production.

In vitro analysis confirmed the ability of the strains to produce siderophore and indole-3-acetic acid (IAA) that are involved in plant growth promotion. In addition, both strains were able to acidify growth media containing glucose.

Figure 2:
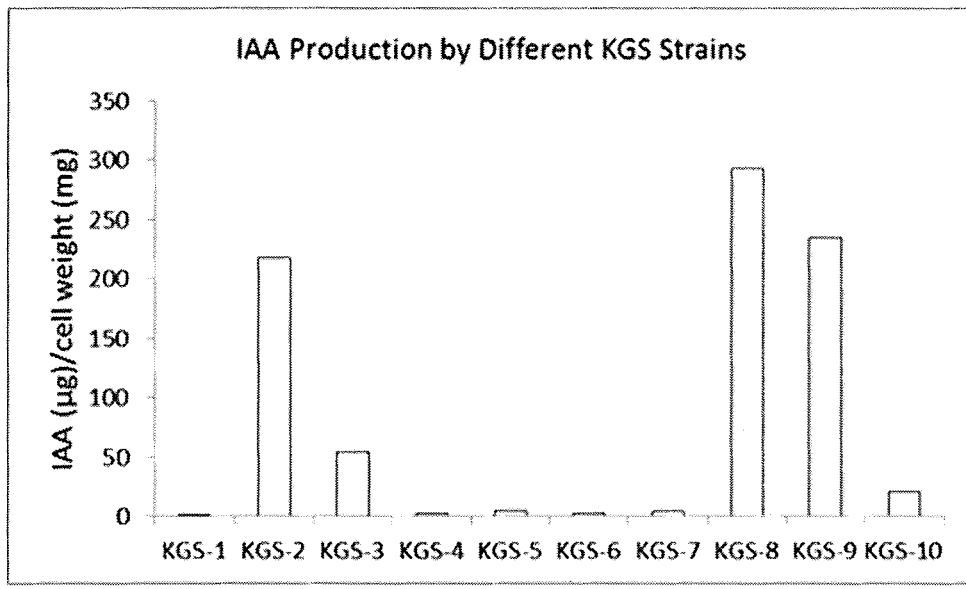
FIG. 2 is a bar graph showing IAA production by different KGS strains.

IAA Assay:

The strains were grown on YEM+0.1% tryptophan overnight. 2 mL of culture was collected and centrifuged. The cell pellet was weighed. Salkowski reagent was then mixed with the supernatant, incubated for 70 minutes and $A_{530}$ reading was obtained. The reading was compared to a standard curve to obtain the concentration of IAA produced. Then, the concentration of IAA produced/cell weight was calculated. The amount of IAA produced was normalized to cell weight. As can be seen in FIG. 2, strains KGS-2, KGS-8 and KGS-9 produced the largest amounts of IAA.

Siderophore Assay:

Bacteria were grown overnight in M9+50 mM glucose. The cells were pelleted and washed 2 times in sterile water. The cells then, were streaked onto CAS plated made with modified M9 base without iron. Results are shown in Table 1.

Example 4—Canola Growth Promotion

The bacteria used for inoculum were grown overnight in LB media at 30° C. for pouch studies under laboratory conditions. The cells were pelleted and washed twice with water. Each canola seed was inoculated (the same day it was planted) with approximately $10^8$ cells/seed.

Figure 3:
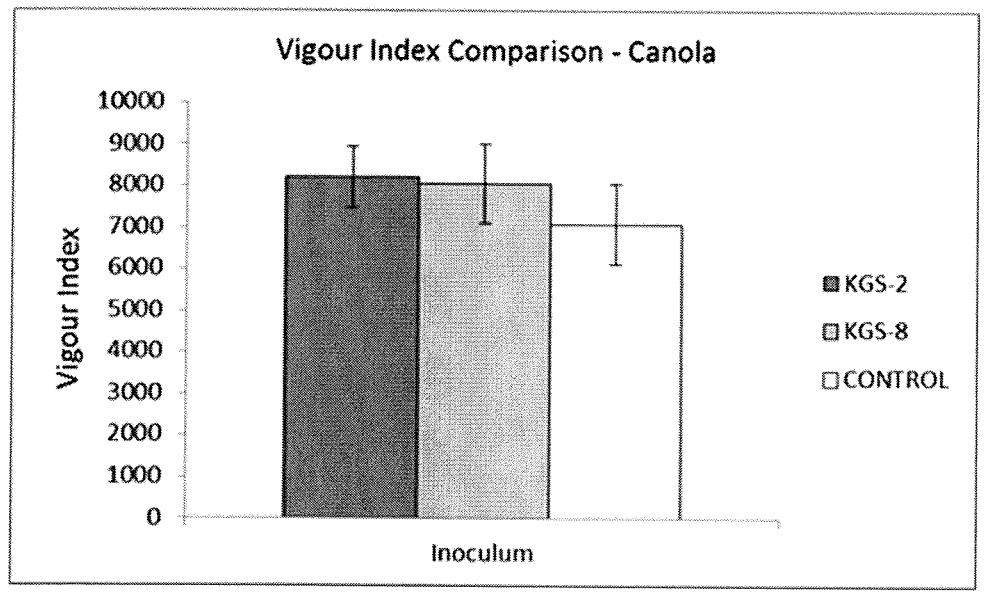
FIG. 3 is a bar graph comparison of vigour index of canola seeds inoculated with KGS-2 or KGS-8.
Figure 4:
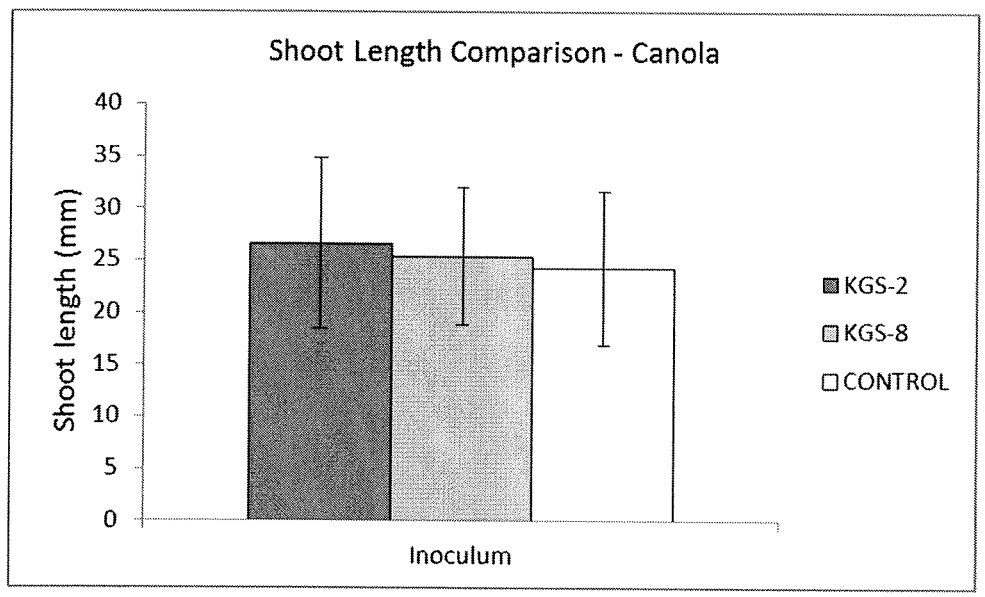
FIG. 4 is a bar graph comparison of shoot length of canola plants grown from seeds inoculated with KGS-2 or KGS-8.
Figure 5:
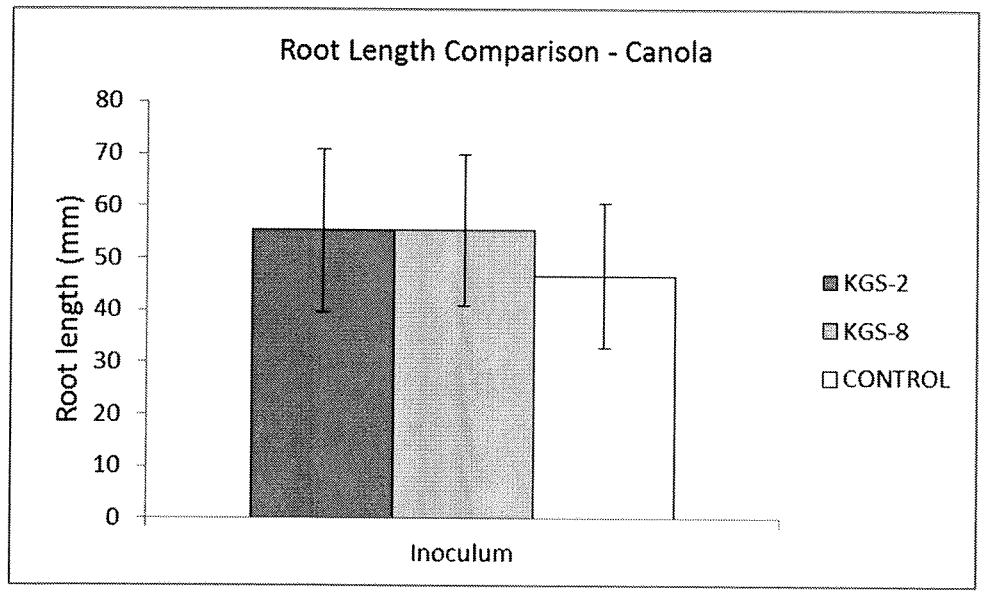
FIG. 5 is a bar graph comparison of root length of canola plants grown from seeds inoculated with KGS-2 or KGS-8.

The results are shown in FIGS. 3 to 5. As can be seen in FIG. 5, the roots of canola plants grown from inoculated canola seed are significantly longer than the non-inoculated control.

Furthermore, as shown in FIG. 3, the seeds inoculated with KGS-2 also have a significantly higher vigour index value (p<0.05) compared to uninoculated plants. The seeds inoculated with KGS-8 also showed an increase in vigour index compared to uninoculated plants.

Figure 6:
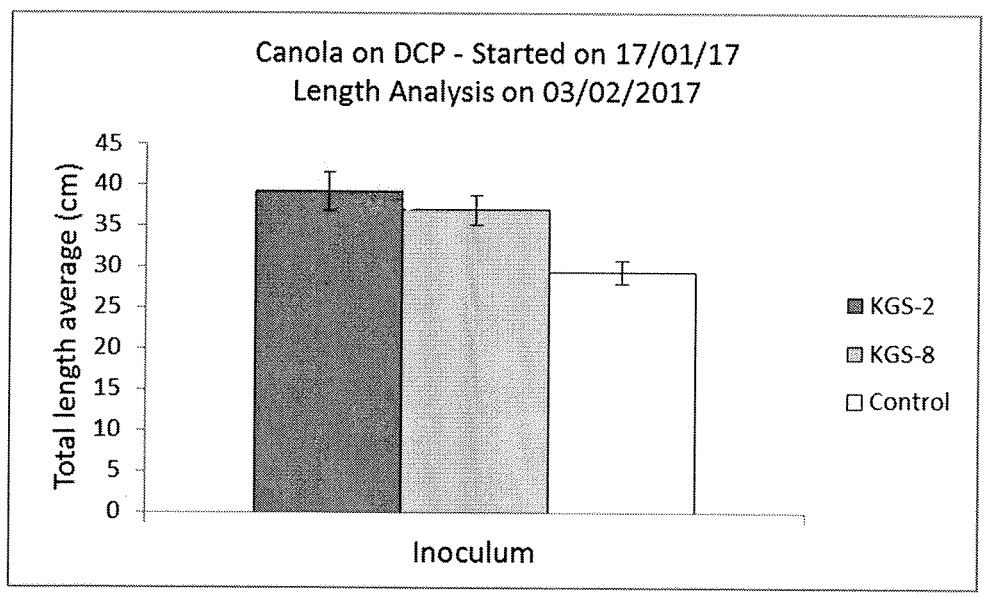
FIG. 6 is a bar graph comparison of total length of canola plants grown from seeds inoculated with KGS-2 or KGS-8 with Dicalcium Phosphate (DCP) as the P source.

The inoculated plants are significantly longer compared to uninoculated plants when DCP is the major source of phosphorus supplied. As shown in FIG. 6, approximately 2.5 weeks after seeding and inoculation, the canola plants inoculated with KGS-2 and KGS-8 are significantly longer than uninoculated plants by approximately 33.78% and 25.85% respectively.

Figure 7:
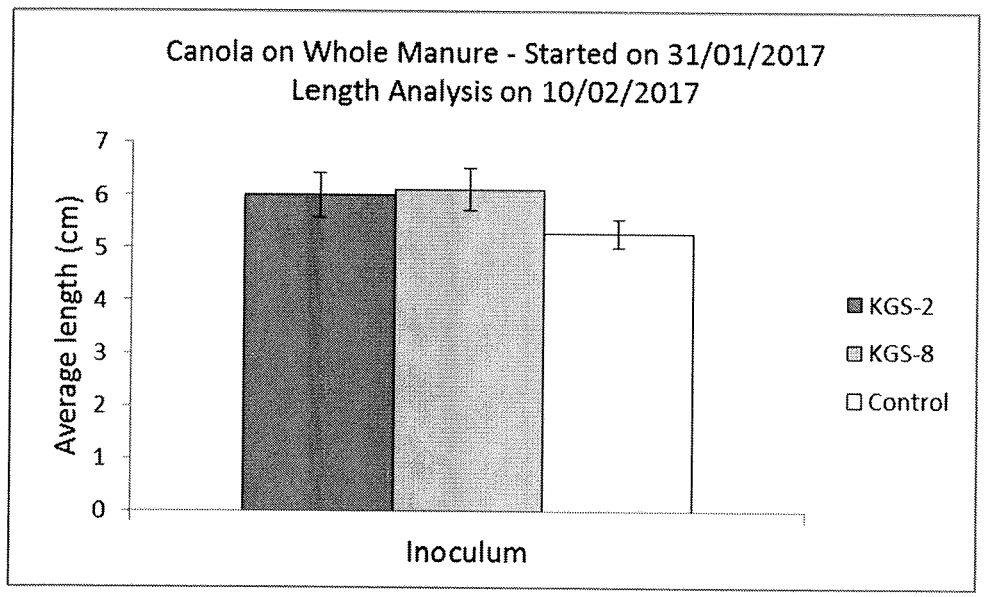
FIG. 7 is a bar graph comparison of total length of canola plants grown from seeds inoculated with KGS-2 or KGS-8 with hog manure as the P source.

As shown in FIG. 7, similar trends were observed on plants that were fertilized with hog manure. Approximately 1.5 weeks after seeding and inoculation, the plants inoculated with KGS-2 and KGS-8 are approximately 13.21% and 15.10% longer than uninoculated plants respectively when grown on manure. This confirms that the effect on plant growth by KGS-2 and KGS-8 is not reliant on the source of the phosphorus being DCP.

Example 5—Corn Growth Promotion

Figure 8:
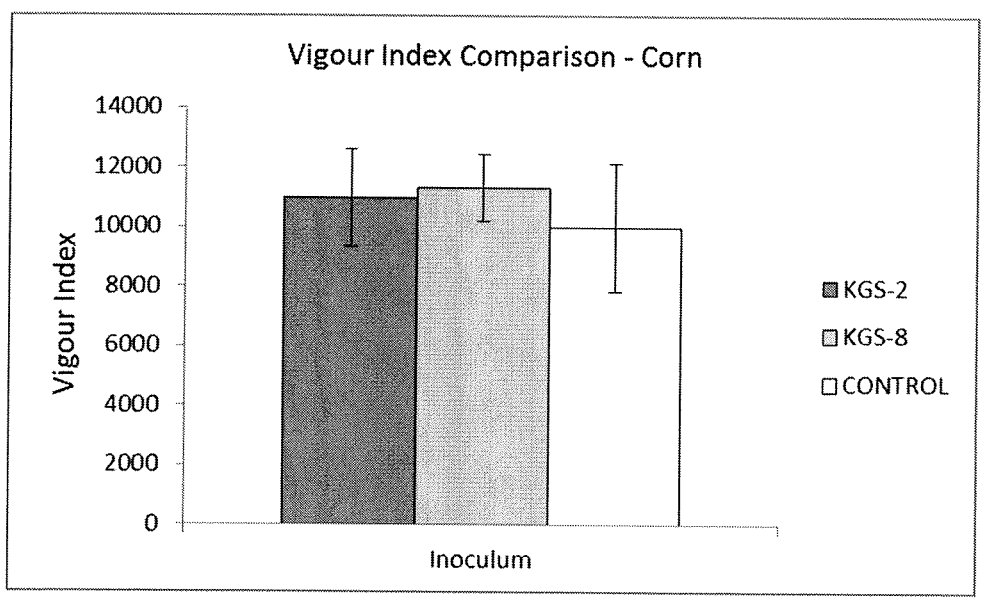
FIG. 8 is a bar graph comparison of vigour index of corn seeds inoculated with KGS-2 or KGS-8.
Figure 9:
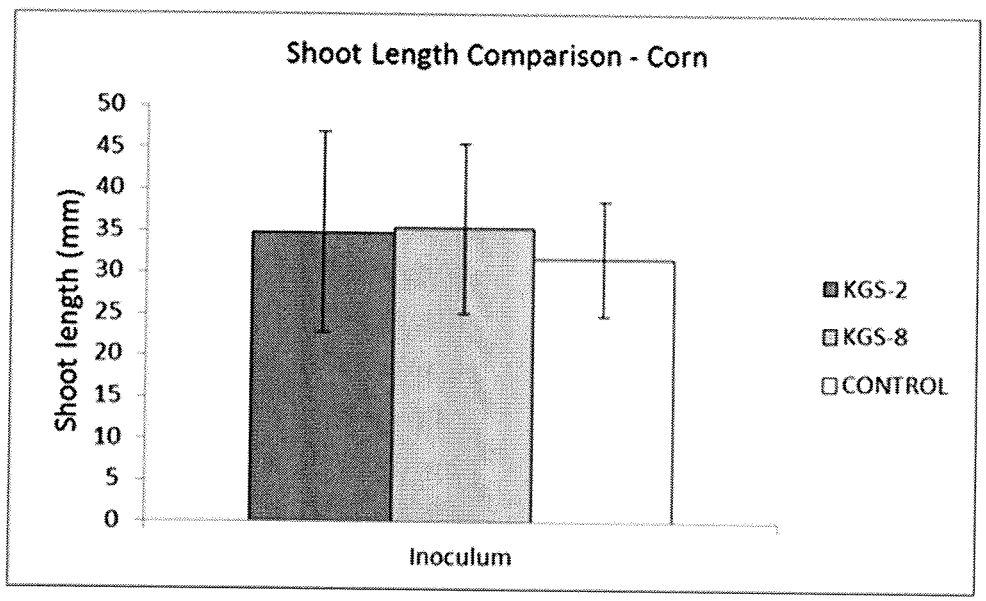
FIG. 9 is a bar graph comparison of shoot length of corn plants grown from seeds inoculated with KGS-2 or KGS-8.
Figure 10:
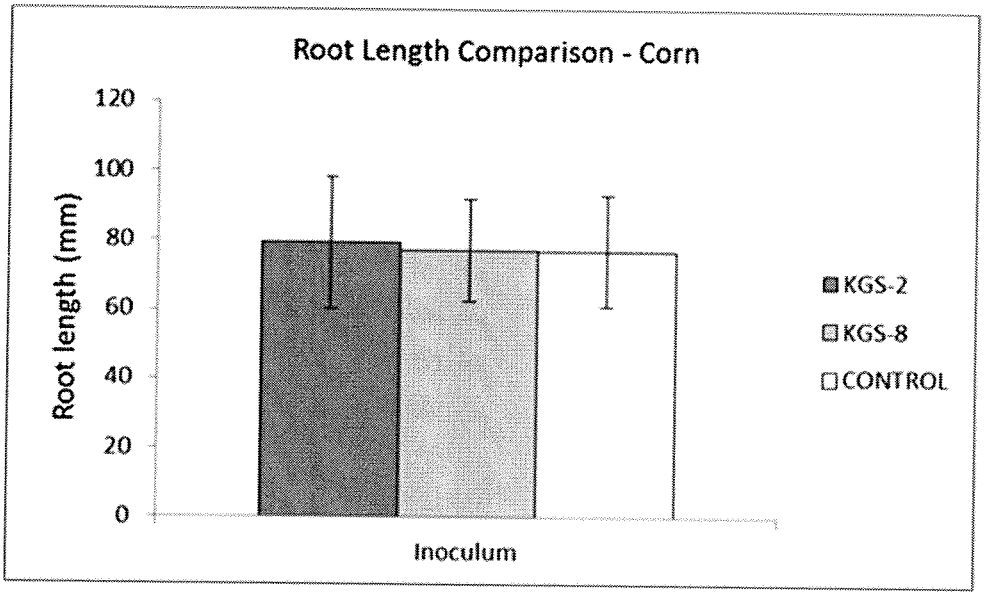
FIG. 10 is a bar graph comparison of root length of corn plants grown from seeds inoculated with KGS-2 or KGS-8.
Figure 11:
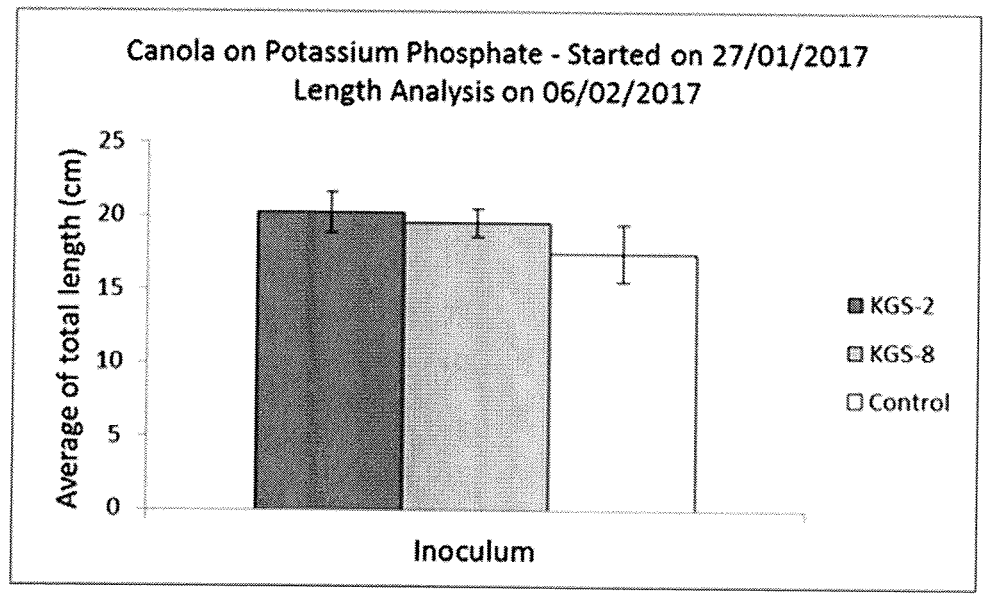
FIG. 11 is a bar graph comparison of total length of corn plants grown from seeds inoculated with KGS-2 or KGS-8 with Potassium Phosphate as the P source.

For corn plants grown from corn seeds inoculated with either KGS-2 or KGS-8 and uninoculated control as described above, there was no significant difference in germination, root, shoot, and weight of seedlings between inoculated and uninoculated control. However, the trend of longer shoot (FIG. 9) and higher value of vigour index (FIG. 8) was observed in the inoculated seeds compared to the control seeds (p>0.05).

The plants that are inoculated with KGS-2 and KGS-8 are significantly longer than uninoculated ones when DCP, struvite, or potassium phosphate (a soluble phosphate compound) was supplied as the major source of phosphorus for plant growth:

Corn Grown with DCP as the Major Source of Phosphorus:
Approximately 2.5 weeks after seeding and inoculation, the plants inoculated with KGS-2 and KGS-8 are approximately 28.24% and 15.35% longer than uninoculated ones respectively.

Corn Grown with Struvite as the Major Source of Phosphorus:
Approximately 1.5 weeks after seeding and inoculation, the plants inoculated with KGS-2 and KGS-8 are approximately 30.77% and 18.62% longer than uninoculated ones respectively.

Figure 12:
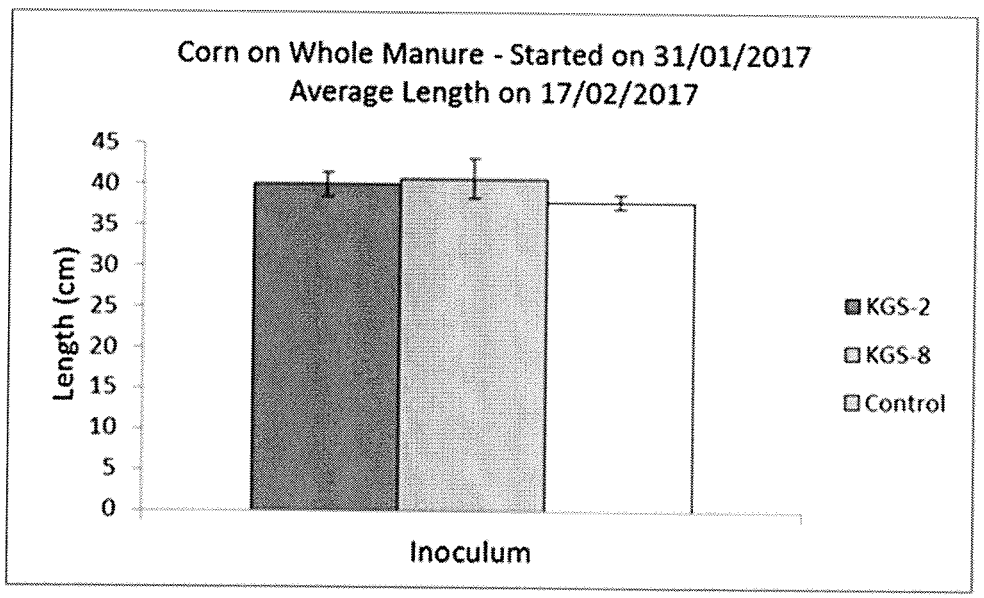
FIG. 12 is a bar graph comparison of total length of corn plants grown from seeds inoculated with KGS-2 or KGS-8 with hog manure as the P source.

Corn Grown with Potassium Phosphate as the Major Source of Phosphorus:
As shown in FIG. 12, approximately 1.5 weeks after seeding and inoculation, the plants inoculated with KGS-2 and KGS-8 are approximately 32.47% and 13.64% longer than uninoculated ones respectively.

Figure 15:
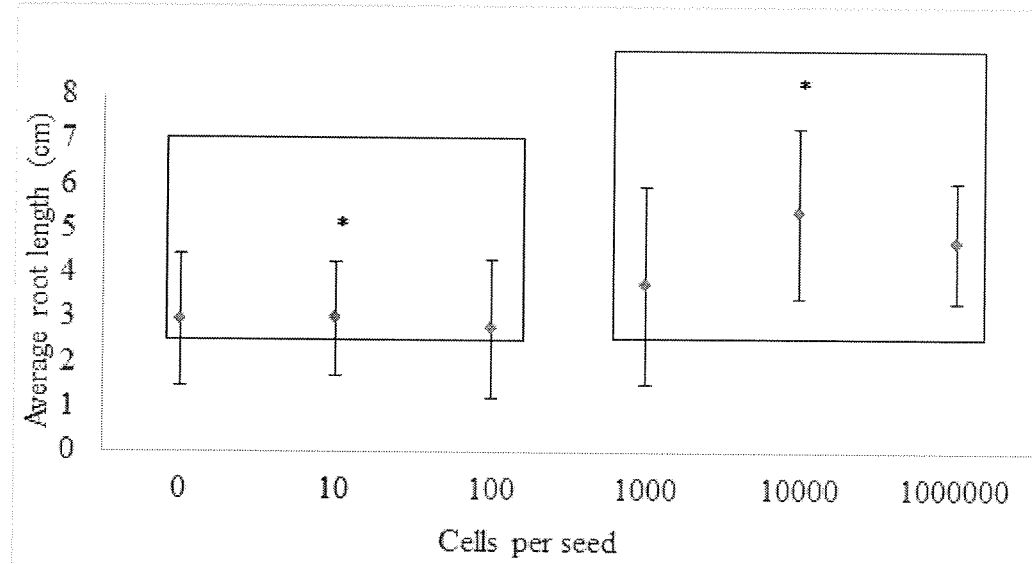
FIG. 15 shows dose response of wheat to KGS-2.

Corn Inoculated with Either KGS-2 or KGS-8 and Uninoculated Control.
Referring to FIG. 15, statistical analysis (Student's t-test) showed that the observed difference between inoculated and uninoculated corn plants is significant, as discussed below. The difference between KGS-2 and KGS-8 inoculated plants is not statistically significant, indicating both strains are equally effective.

Figure 16:
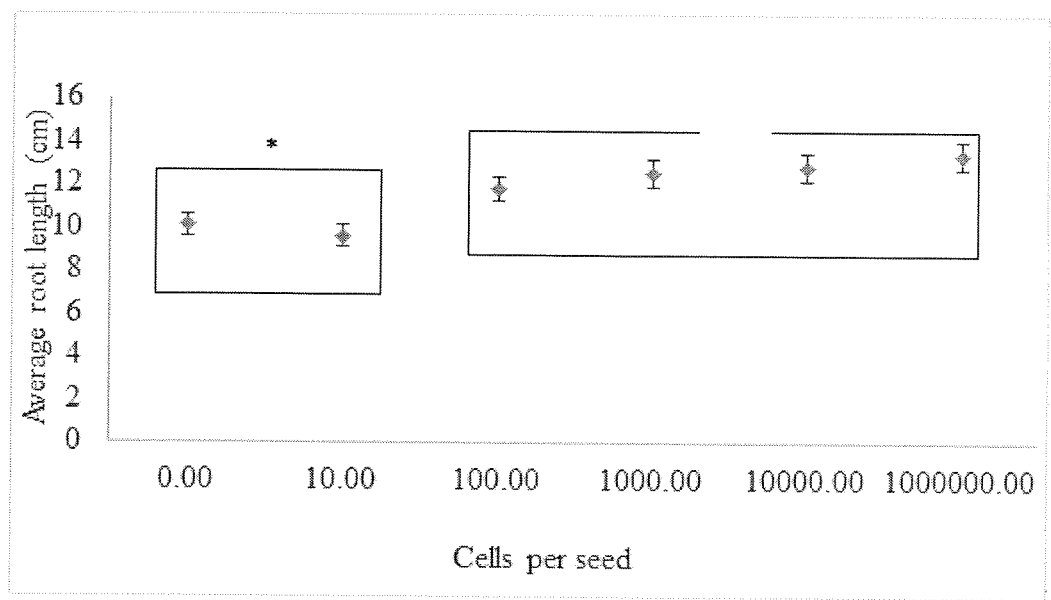
FIG. 16 shows dose response of canola to KGS-2.

Corn Inoculated with Either KGS-2 or KGS-8 and Uninoculated Control.
Referring to FIG. 16, statistical analysis (Student's t-test) showed that the observed difference between inoculated and uninoculated canola plants is significant, as discussed below. The difference between KGS-2 and KGS-8 inoculated canola plants is not statistically significant, indicating both strains are equally effective.

The same result was also seen in canola plants grown on potassium phosphate.

Example 6—Bacterial Viability Data

In order to apply the cells to field work, KGS-2 needed to be grown to very high cell densities and had to be shown to be stable for a significant length of time. In order to get a sense of viability over time, cell viability was evaluated at one and four weeks for KGS-2 cells grown in the fermenter and placed in a refrigerator. This indicated that ~25% CFU/ml is lost in 4 weeks, therefore these cultures are rather stable.

Figure 14:
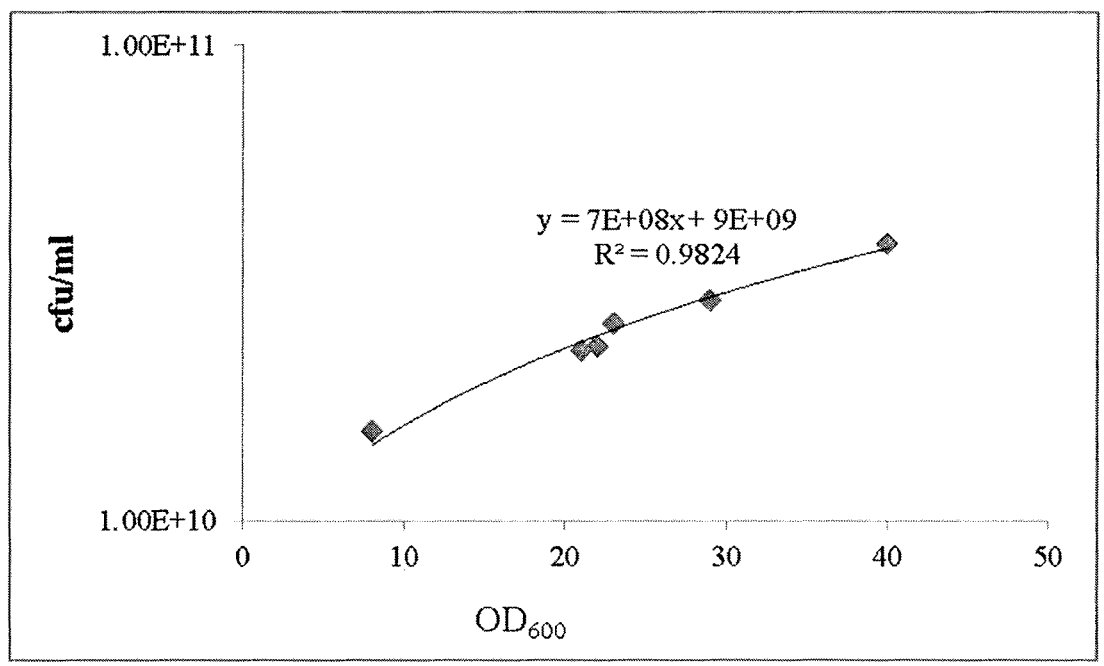
FIG. 14 is a comparison of Optical Density at 600 nm ($OD_{600}$) to colony forming units per milliliter (CFU/ml) of KGS-2.

After the fermenter used to grow KGS-2 was optimized, higher and higher cell concentrations were achieved. There were concerns that CFU/mL (viable cells/mL) may decrease as they were grown to higher densities. CFU/mL can decrease at high-density due to cell death, cells changing in dimensions, or the production of other compounds. FIG. 14 shows that of the early experiments measured, $OD_{600}$ (optical density of a sample measured at 600 nm) correlates quite well to CFU/mL. This is good for an inoculum product, as it means making double the weight is actually making double the inoculum.

Example 7—Seed Vigor Index

Table 2 shows the SVI results of treated (KGS-2) and untreated (Control) seeds for barley, winter and spring wheat, canola, soybean, corn, fava, flax and alfalfa. It can be observed that the highest SVI improvement was obtained with spring wheat (53%) at p-value of 0.05. An approximate 50% change in SVI is a profound change that could drastically affect spring wheat yield in field trials.

KGS-2 performed quite well in comparison with a SVI increase of ~50% on spring wheat. Typically, neither the SVI in the literature nor the ones done within this study showed significant changes in germination rates; the majority of the differences seen in SVI can be attributed to changes in root and seedling length.

Example 8—Dose Response

The same conditions and methodology were used for dose response but in this case the growth pouches had dynamic concentrations of KGS-2. FIG. 15 shows that the effective dose on wheat under controlled lab conditions is $10^3$-$10^4$ cells. A t-test shows that 0, 10, 100 group together, and $10^3$, $10^4$, $10^6$ are another group at a p-value <0.05. FIG. 16 shows the dose response of canola. Treatments of 0 and 10 KGS-2 cells on canola form one group based on t-tests, all higher (100 to $10^6$) cell treatments form the other. The two groups are distinguishable at a p-value<0.05.

Overall the lab work indicates an interaction with KGS-2 with a variety of commercially relevant crops especially with spring wheat. There is also a relatively strong interaction with KGS-2 when compared to the seed vigor indexes within the literature, clearly the increased size of seedlings would be highly beneficial to crops under field conditions.

In this experiment, inoculum was sprayed on the crop after the crop emerged. The purpose of this trial was to test two factors: i) the dose response of bacterial treatments to wheat and canola yields; ii) to test the effect of low phosphate on differing doses.

Each plot was 2.5 m by 4 m, and the testing assessed two main variables, explained as follows:
Dose response from $10^5$ to $10^9$ cells per seed
Treatment 1 or Control (no treatment)
Treatment 2 ($10^5$ cells added) to Treatment 6 ($10^9$ cells added)
Normal fertilization low phosphate (A) versus normal fertilization (B)

Figure 17:
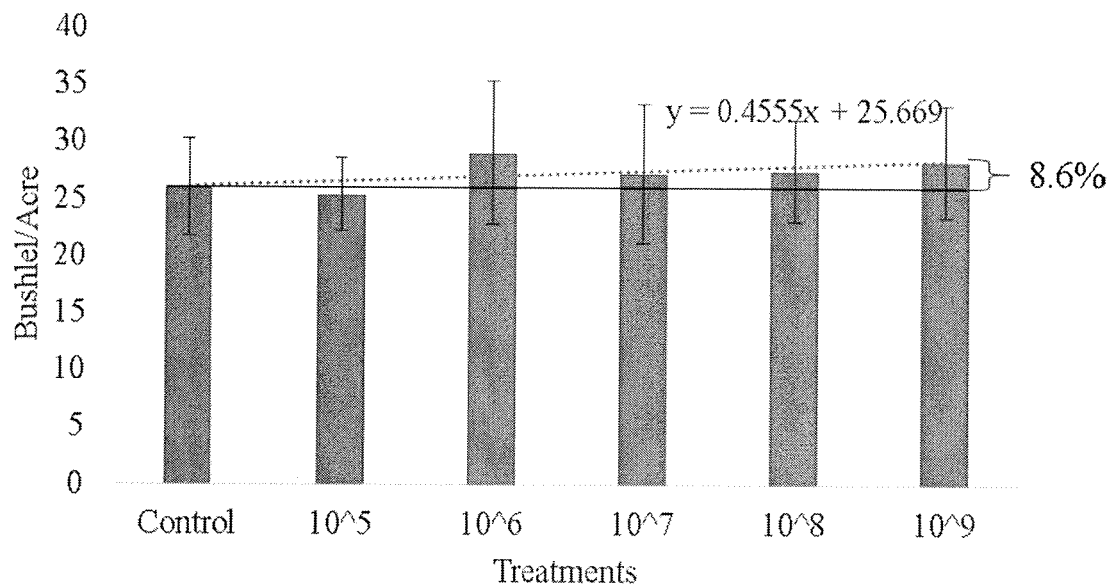
FIG. 17 shows effect of increasing KGS-2 on wheat growth.
Figure 18:
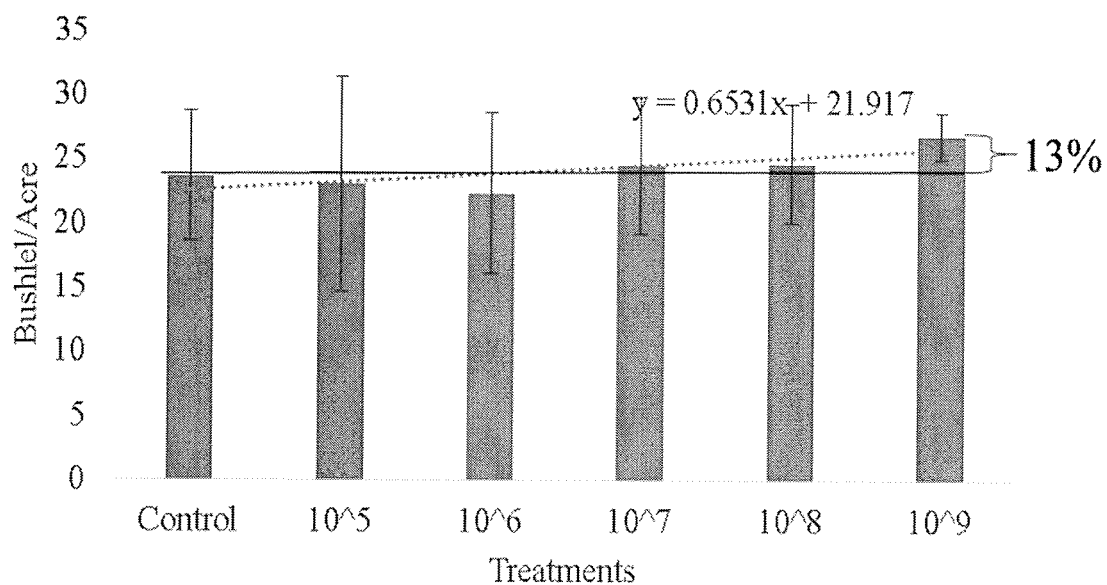
FIG. 18 shows effect of increasing KGS-2 on wheat growth under low phosphate conditions.

Wheat shown in FIG. 17 shows 8.6% improvement in yield between control and strongest treatment. When the low phosphate treatment is considered an even larger improvement is seen, as FIG. 18 shows ~13% yield improvement between control and strongest treatment.

It appears that the highest treatment in the low phosphate condition has a similar value to the untreated properly fertilized condition, therefore it appears high doses of KGS-2 may functionally replace ~35 lbs/acre of phosphate. KGS-2 could be used offset fertilizer costs in the spring when farmers are becoming the most financially constrained.

Statistical analysis system (SAS) analysis showed that wheat had a linear relationship (0.0167<0.05) between adding more bacteria and yield, indicating that the effect of adding a higher KGS-2 concentration did not show saturation. Of important note: the only way these models could provide significant results was when the control was removed, as the control was assumed to have zero bacteria. Later results showed that this is unlikely, and there is probably bleed over effects from nearby plots. If the control is removed and the best fit line added there is an estimated 16% yield difference between wheat $10^5$ and $10^9$.

Example 9—Bacterial Population at Carman Using QPCR

As shown in FIGS. 19 and 20, In order to track bacterial populations in soil primer sets were developed. The primer set used was specific for the *Pseudomonas* genus (Pse435F ACTTTAAGTTGGGAGGAAGGG (SEQ ID NO:1); Pse686R ACACAGGAAATTCCACCACCC (SEQ ID NO:2); probe Pse449 ACAGAATAAGCACCGGCTAAC (SEQ ID NO:3)) (Li et al. 2013). The genus specific set worked well and was extremely sensitive in soil and pure culture experiments. The soil samples are extremely heterogeneous with there being high variability between soil sample replicates which obfuscates any change in total *Pseudomonas* population between time points/treatments.

To further investigate the population level of KGS-2, a highly specific probe was used (p2f-JessFlorc ATCTC-CGAAGAGATCGGCCT (SEQ ID NO:4); p2r-JessFlorc ACGCGGGCTTTCTTCTCTTT (SEQ ID NO:5); probe2-JessFlorc GTTGCAGTGATCAAGGTTGGCGCTGGTTC (SEQ ID NO:6)). This probe is specific to KGS-2 or highly related strains (UW4 for instance). Unfortunately, this method was not sensitive enough, only detecting KGS-2 concentrations of 105 or higher, to recognize it in soil DNA extracts.

These primers target the cpn60 gene region that is specific to KGS-2, KGS-8 and *Pseudomonas* sp. UW4. The primers targeting cpn60 were chosen due to their ability to provide similar results to whole genome sequencing (Verbeke at al. 2011). The BLAST primer design was utilized to obtain the optimal primers.

The sequences of *Pseudomonas putida, Bacillus* and *Clostridia*, were utilized as outside groups that the primers will not be able to target. This is because *Pseudomonas putida* and *Clostridium* are possible contaminants for the analysis in the laboratory where the research was conducted. Furthermore, *P. putida*, as a relative of *P. jessenii* confirms the specificity of the primers. The genus *Bacillus* also contains calcium solubilizing species, which is why it was also used as an outside group for the primer design. Once the primers were designed, BLAST was then utilized to confirm that the primers did not detect organisms than KGS-2, KGS-8, and *Pseudomonas* sp. UW4.

For quantification of the number of bacteria in the *Pseudomondas* genus, the following primers and probes were used with IQ supermix (Pse435F ACTTTAAGT-TGGGAGGAAGGG (SEQ ID NO:1); Pse686R ACACA-GGAAA TTCCACCACCC (SEQ ID NO:2); probe Pse449 ACAGAATAAGCACCGGCTAAC (SEQ ID NO:3)). In order quantify the strain specific bacteria numbers the following probes and primers were used with the same method and temperatures as above (p2f-JessFlorc ATCTC-CGAAGAGATCGGCCT (SEQ ID NO:4); p2r-JessFlorc ACGCGGGCTTTCTTCTCTTT (SEQ ID NO:5); probe2-JessFlorc GTTGCAGTGATCAAGGTTGGCGCTGGTTC (SEQ ID NO:6)).

The above-listed primers and probes can be combined for a multiplex reaction.

Figure 21:
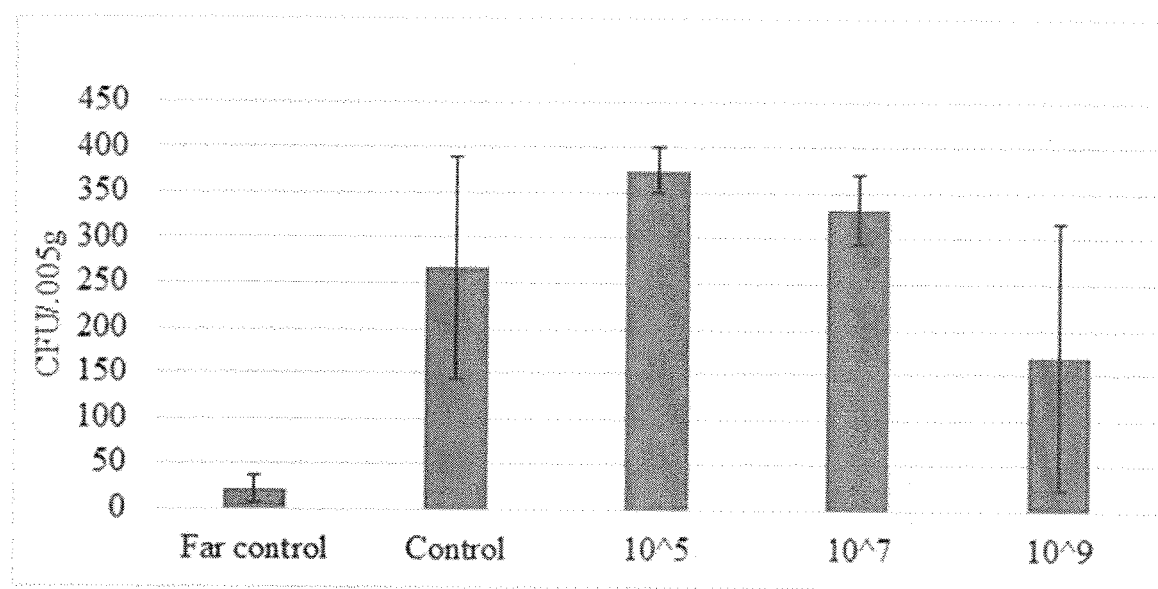
FIG. 21 shows number of bacteria recovered from wheat stems.

QPCR Mixture
5.5 ul of IQ supermix
250 nmol each primer
250 nmol probe
1 ng template
Add H2O to a final volume 10 ul
QPCR Reaction
Denaturing 95 for 3 min
35× the following 2 steps:
1) 15 seconds denaturing
2) 30 seconds annealing at 64° C.
3) Read plate
Then hold at room temperature Example 10—Endophytic Bacterial Population at Carman Using Plating Based on our genome analysis, and the presence of phenyl acetic acid catabolism we suspected KGS-2 of being an endophytic organism. FIG. 21 shows that on average the number of phosphate solubilizing bacteria within the wheat stem are significantly higher in the trial compared to control wheat taken from 500 m away.

The number of bacteria do not differ statistically by treatment (control, $10^5$, $10^9$), likely because all plants were fully colonized by bacteria at the time of sampling, even the control due to bleed over. The colonies derived from the far control also did not show zones of clearing consistent with phosphate solubilization. The colonies derived from the Carman trial showed similar phosphate solubilization to KGS-2 and tested positive for amplification when the specific primer sets were used. This indicates that the colonies derived from the stems are KGS-2 or highly related to it.

A different relationship is seen with canola which recruits organisms (likely a related *Pseudomonas* based on morphology and molecular tests) into the stems. Even the colonies from a control plot 500 m away from the test plots demonstrated a good ability to solubilize insoluble phosphate. Statistically all of the treatments, including the far control, are the same (p-value>0.05). Fewer colonies tested positive for being highly related to KGS-2 in the far control, suggesting that there may be similar organisms in the environment, and that the canola is effective at recruiting them.

The study was conducted in a greenhouse, and sunshine mix #1 (Sun Gro) was utilized as the growth medium. The plants were seeded at the rate of 10 seeds/pot (pots with 6 inches diameter were utilized) and inoculated (108 C FU of KGS-2/seeds) on the same day. The experiments were done in triplicates. The above ground plant material from the emerged plants were then sampled every week (starting the week after seeding), surface sterilized, aseptically crushed, and spread onto standard Pikovskaya (PVK) agar plates containing 50 mM glucose. Approximately 4 different types of colony, based on morphology could be observed on PVK plates. Representative colonies (based on colony morphology) from each type of colonies that were present on PVK were utilized as templates for PCR analysis utilizing primers that are specific for KGS-2.

In canola, endophytes were present in KGS-2-inoculated and non-inoculated control plants as early as 1 week after seeding and inoculation (FIG. 1 and Table 1). There are several different types of colonies in a single plate (replicate) based on the morphology such as relative size, color, and margin (irregular and circular The experiments were designed to provide qualitative confirmation that KGS-2 was present as endophytes in host canola plants. The data showed that KGS-2 cells were present as a major proportion of the consortium of endophytes only from the plants that were inoculated with KGS-2 and not the non-inoculated control plants.

The presence of endophytic KGS-2 cells was confirmed in corn, as with canola, by PCR as early as 1 week post-seeding and inoculation. Positive PCR results were only obtained from inoculated corn plant samples. PCR results indicated that KGS-2 cells were present in the sample of water used in the final wash step of surface sterilization. This may be due to the release of endophytic KGS-2 cells from the damaged plant tissues to the water during the final washing step of surface sterilization. DNA extracted from selected colonies taken from the uninoculated controls did not bind and amplify using the KGS-2 specific primers.

In wheat, the presence of endophytic cells was observed 1 week post-seeding and inoculation. However, PCR analysis showed that none of these colonies were KGS-2 cells. Instead, the presence of endophytic KGS-2 cells was confirmed 2-weeks post seeding and inoculation.

Although the experiment was designed to only qualitatively confirm the presence of endophytic KGS-2 cells, the percentage of endophytes isolated from canola that were putative KGS-2 cells was estimated (i.e. on the basis of colony characteristics). Combining the PCR and colony count data, an estimated 71.5±9.6% of the endophytes isolated from inoculated plants were KGS-2 cells (the inoculum), while the uninoculated plants were free of KGS-2 cells Example 11—Dry Formulation The purpose of this experiment was to demonstrate the possibility of preparing a dry formulation for cells of KGS-2. We do not present an optimized process, but one that will form the preliminary bases for the development of an optimized formulation. We show that cells of KGS-2 will effectively bind to Diatomaceous Earth (DE) at levels of $10^8$ to $10^9$ cells per gram of DE that can be dried to produce a dried granular material that can be used as a dry inoculum for delivery of the cells to the field. Once dried the DE+bacteria will subsequently release approximately 5% of the cells as viable colony forming units (CFU) upon rehydration in excess distilled water after 5 minutes of vigorous shaking.

This indicates that a minimum of 5% of the cells survived the drying process. This may be an underestimation. For example, it may be that the detachment protocol was inefficient and most of the bacteria were viable, but not released. Alternatively, the DE used contained a significant amount of fine particles that did not settle effectively, and it is possible that these fines had each several bacteria bound, which were transferred to the dilutions for CFU determination; as such 1 CFU may represent several bacteria adhering to a common fine particle of DE. Pesenti-Barili et al., 1991, did report between 10-95% viability (based on recovered CFU) depending on the matrix used.

Preparation of 1 Gram of Dry Inoculum of KGS-2 Utilizing Diatomaceous Earth (DE):
(Note: this protocol can be up-scaled depending on the required amount of dried inoculant is needed)
1. Prepare 1 gram of sterile DE (AgReady) by autoclaving
2. Transfer DE to a sterile falcon tube (15 mL)
3. Grow KGS-2 cells overnight in R2M+5 g/L glucose (see medium description below)
4. Obtain $OD_{600}$ reading and calculate the concentration (CFU/mL) of the cells
5. On the basis of the previous point, use an aliquot of a volume corresponding to $1\times10^8$ of KGS-2 cells
6. Centrifuge the cells and discard the supernatant
7. Resuspend the cells with 0.5 mL of ½ R2M containing 2.5 g/L of glucose (media recipe is on the following page)
8. Apply the cell suspension to 1 gram of sterile DE and shake vigorously with tightly closed cap
9. Slightly loosen the cap and let the inoculum dry in room temperature overnight (15-24 hours will be sufficient)

Extra Notes:
a. 0.5 mL of liquid/gram of DE is sufficient for dry inoculum preparation
b. $1\times10^8$ cells or less should be applied to 1 gram of DE for dry inoculum preparation. If more than $1\times10^8$ cells were to be applied to 1 gram of DE, the extra cells are at risk of not being attached to DE (see the next page). The carrying capacity of 1 gram of this DE is only $10^8$ cells.
c. R2M is modified Ramsay medium. This medium contains $2\times MgSO_4$. ½ R2M+2.5 g/L glucose was prepared by diluting R2M+5 g/L glucose with Milli-Q H2O
d. Table 1 shows the composition of 1 gram of dry inoculum, including minerals from the R2M medium.
e. Use the same ratio of liquid and DE to upscale the dried inoculant production Recovery of KGS-2 cells from the inoculum $1.04\times10^8$ and $1.04\times10^9$ of KGS-2 cells (confirmed by viable plate count method) were obtained from the culture that was grown overnight in R2M+5 g/L glucose. The appropriate amount of culture was transferred into sterile Eppendorf tubes and the supernatant was removed by centrifugation at 10,000×g for 1 minute). The cells were then suspended in 0.5 mL of ½ R2M containing 2.5 g/L glucose (Prepared by diluting 250 µL of R2M+5 g/L glucose with 250 µL of sterile millQ $H_2O$). The cell suspensions were applied to individual aliquots of DE (1 g each) aseptically. For the negative control experiment confirming lack of contamination, 0.5 mL of ½ R2M containing 2.5 g/L glucose without KGS-2 was applied aseptically to sterile 1 gram of DE.

For each test of the protocol, each inoculum (DE mixed with cell suspension or medium with no KGS-2) was then shaken vigorously to ensure uniform distribution of cells on DE. The bacterial cells were left to dry by leaving the falcon tubes standing on the rack overnight at room temperature with the caps slightly loosened (still keeping the inside sterile).

The next day (15-24 hours), the dried bacteria-DE mixtures were transferred into individual fresh sterile 15 mL falcon tubes. 10 mL of sterile $ddH_2O$ was added to each tube. The tubes were shaken vigorously (the caps were tightly closed). This was followed by further shaking utilizing a plate shaker (Tektator V) set at the maximum speed at 14,000 rpm for 5 minutes. The supernatant samples were obtained for serial dilutions (in sterile water) and spread plating to calculate the number of viable bacteria recoverable in the supernatant (Tables 3 and 4).

The plates spread with dilution samples of the supernatant from the negative control (1 g of DE+500 µL of sterile medium as indicated above) were free of bacteria as expected. 5.7±0.9% and 4.7±0.4% of the bacteria were recovered from the inocula prepared utilizing $1.04\times10^8$ and $1.04\times10^9$ of KGS-2 cells respectively (Table 3 and 4). This suggests that most of the bacteria may still be attached to DE and were not released after resuspension in water followed by shaking. In addition, the bacteria that were recovered from the supernatant may have been attached to the surface of DE instead of immobilized in the pores. This indicates that multiple washes or utilization of other methods may be necessary to completely release the bacteria from DE (for analysis purposes). Or, if there is indeed low viability, a different matrix be tested as well as the use of a protective solution.

From these results, it is hypothesized that when the developed dry inoculum is utilized in the field, the bacteria will be released gradually through the watering of the plants. In addition, when the bacteria multiply, the progeny cells may be released to the soil.

The scope of the claims should not be limited by the preferred embodiments set forth in the examples but should be given the broadest interpretation consistent with the description as a whole.

REFERENCES

Ali S, Charles T C, & Glick B R. 2012. Delay of flower senescence by bacterial endophytes expressing 1-aminocyclopropane-1-carboxylate deaminase. Journal of Applied Microbiology. 113, 1139-1144.

Andreote, F. D., de Araújo, W. L, de Azevedo, J. L., van Elsas, J. D., da Rocha, U. N., and van Overbeek, L. S. 2009. Endophytic colonization of potato (*Solanum tuberosum* I.) by a novel competent bacterial endophyte, *Pseudomonas putida* strain P9, and its effect on associated bacterial communities. Appl. Environ. Microbiol. 75(11):3396-3406.

Basha S A, Sarma B K, Singh D P, Annapurna K, & Singh U P. 2006. Differential methods of inoculation of plant growth-promoting rhizobacteria induce synthesis of phenylalanine ammonia-lyase and phenolic compounds differentially in chickpea. Folia Microbiologica. 463-468.

Bashan Y, de-Bashan L E, Prabhu S R, & Hernandez J P. 2014. Advances in plant growth-promoting bacterial inoculant technology: formulations and practical perspectives (1998-2013). Plant and Soil. 378, 1-33.

Bashan Y, Kamnev A A, & de-Bashan L E. 2013. Tricalcium phosphate is inappropriate as a universal selection factor for isolating and testing phosphate-solubilizing bacteria that enhance plant growth: a proposal for an alternative procedure. Biology and Fertility of Soils. 49, 465-479.

Beneduzi et al. 2012. Plant growth-promoting bacteria (PGPB): Their potential as antagonists and biocontrol agents. Gen. Mol. Biol. 35(4):1044-1051.

Blunt W, Dartiailh C, Sparling R, Gapes D, Levin D B, & Cicek N. 2017. Microaerophilic environments improve the productivity of medium chain length polyhydroxyalkanoate biosynthesis from fatty acids in *Pseudomonas putida* LS46. Process Biochemistry.

Buch A, Archana G, & Kumar G N. 2008. Metabolic channeling of glucose towards gluconate in phosphate-solubilizing *Pseudomonas aeruginosa* P4 under phosphorus deficiency. Research in microbiology. 159, 635-642.

Cheng Z, Park E, & Glick B R. 2007. 1-Aminocyclopropane-1-carboxylate deaminase from *Pseudomonas putida* UW4 facilitates the growth of canola in the presence of salt. Canadian Journal of Microbiology. 53, 912-918.

Devi, K. A., Pandey, G., Rawat, A. K. S., Sharma, G. D., and Pandey, P. 2017. The endophytic symbiont—*Pseudomonas aeruginosa* stimulates the antioxidant activity and growth of *Achyranthes aspera* L. Front. Microbiol. 8(1897): 1-14.

Ditta & Khalid A. 2016. Bio-organo-phos: a sustainable approach for managing phosphorus deficiency in agricultural soils. Organic Fertilizers. 109-136.

Gholami A, Shahsavani S, & Nezarat S. 2009. The effect of plant growth promoting rhizobacteria (PGPR) on germination, seedling growth and yield of maize. International Journal of Biological Life Sciences. 1, 35-40.

Giles C D, Hsu P L., Richardson A E, Hurst M R, & Hill J E. 2014. Plant assimilation of phosphorus from an insoluble organic form is improved by addition of an organic anion producing *Pseudomonas* sp. Soil Biology and Biochemistry. 68, 263-269.

Greenberg B M, Huang X D, Gerhardt K, Glick B R, Gurska J, Wang W, Lampi M, Khalid A, Isherwood D, Chang P, & Wang H. 2007. Field and laboratory tests of a multi-process phytoremediation system for decontamination of petroleum and salt impacted soils. Proceedings of the Ninth International In Situ and On-Site Remediation Symposium. Gavaskar, A R and Silver C F, eds., Batelle Press, Columbus, Ohio.

Ige D V, Akinremi O O, Flaten D N, Ajiboye B, & Kashem M A. 2005. Phosphorus sorption capacity of alkaline Manitoba soils and its relationship to soil properties. Canadian Journal of Soil Science. 85, 417-426.

Jain R & Pandey A. 2016. A phenazine-1-carboxylic acid producing polyextremophilic *Pseudomonas chlororaphis* (MCC2693) strain, isolated from mountain ecosystem, possesses biocontrol and plant growth promotion abilities. Microbiological Research. 190, 63-71.

Juan C, Pena C, & Oliver A. 2017. Host and pathogen biomarkers for severe *Pseudomonas aeruginosa* infections. The Journal of Infectious Diseases. 215, S44-S51

Keplinger K O & Hauck L M. 2006. The economics of manure utilization: model and application. Journal of Agricultural and Resource Economics. 414-440.

Khan Z, Roman D, Kintz T, delas Alas M, Yap R, & Doty S. 2014. Degradation, phytoprotection and phytoremediation of phenanthrene by endophyte *Pseudomonas putida*, PD1. Environmental Science & Technology. 48, 12221-12228.

Kong Z & Glick B R. 2017. The role of plant growth-promoting bacteria in metal phytoremediation. Advances in Microbial Physiology.

Kumar A & Rai L C. 2015. Proteomic and biochemical basis for enhanced growth yield of *Enterobacter* sp. LCR1 on insoluble phosphate medium. Microbiological Research. 170, 195-204.

Kumar A, Maurya B R, & Raghuwanshi R. 2015. Characterization of bacterial strains and their impact on plant growth promotion and yield of wheat and microbial populations of soil. African Journal of Agricultural Research. 10, 1367-1375.

Lally, R. D., Galbally, P., Moreira, A. S., Spink, J., Ryan, D., Germaine, K. J., and Dowling. D. N. 2017. Application of endophytic *Pseudomonas fluorescens* and a bacterial consortium to *Brassica napus* can increase plant height and biomass under greenhouse and field conditions. Front. Plant Sci. 8(2193):1-10.

Li L, Al-Soud W A, Bergmark L, Riber L, Hansen L H, Magid J, & Sorensen S J. 2013. Investigating the diversity of *Pseudomonas* spp. in soil using culture dependent and independent techniques. Current Microbiology. 67, 423-430.

Li, X., Geng, X., Xie, R., Fu, L., Jiang, J., Gao, L., and Sun, J. 2016. The endophytic bacteria isolated from elephant grass (*Pennisetum purpureum* Schumach) promote plant growth and enhance salt tolerance of Hybrid Pennisetum. Biotechnol. Biofuels. 9(190):1-12.

Meyer J M. 2000. Pyoverdines: pigments, siderophores and potential taxonomic markers of fluorescent *Pseudomonas species. Archives of Microbiology.* 174, 135-142.

Nehra V & Choudhary M. 2015. A review on plant growth promoting rhizobacteria acting as bioinoculants and their biological approach towards the production of sustainable agriculture. Journal of Applied Natural Science. 7, 540-556.

Parnell J J, Berka R, Young H A, Sturino J M, Kang Y, Barnhart D M, & DiLeo M V. 2016. From the lab to the farm: an industrial perspective of plant beneficial microorganisms. Frontiers in Plant Science. 7.

Patel T K & Williamson J D. 2016. Mannitol in plants, fungi, and plant-fungal interactions. Trends in Plant Science. 21, 486-497.

M. Rajkumar, H. Freitas 2008 Effects of inoculation of plant growth promoting rhizobacteria on Ni uptake by Indian mustard Bioresour. Technol., 99: 3491-3498

Ramsay B A, Lomaliza K, Chavarie C, Dube B, & Ramsay J A, Production of poly(beta-hydroxybutyric-co-beta-hydroxyvaleric) acids, Applied Environmental Microbiology. 56, 2093-2098.

Rodriguez H & Fraga R. 1999. Phosphate solubilizing bacteria and their role in plant growth promotion. Biotechnology Advances. 17, 319-339.

Smyth E M, McCarthy J, Nevin R, Khan M R, Dow J M, O'Gara F, & Doohan F M. (2011). In vitro analyses are not reliable predictors of the plant growth promotion capability of bacteria; a *Pseudomonas fluorescens* strain that promotes the growth and yield of wheat. Journal of Applied Microbiology. 111, 683-692.

Saha et al. 2013. Microbial siderophores: a mini review. J. Basic. Microbiol. 53:303-317.

Taghavi S, Garafola C, Monchy S, Newman L, Hoffman A, Weyens N, Barac T, Vangronsveld J, & van der Lelie D. 2009. Genome survey and characterization of endophytic bacteria exhibiting a beneficial effect on growth and development of poplar trees. Applied and Environmental Microbiology. 75, 748-757.

Verbeke T J, Sparling R, Hill J E, Links M G, Levin D, & Dumonceaux T J. 2011. Predicting relatedness of bacterial genomes using the chaperonin-60 universal target (cpn60 UT): application to *Thermoanaerobacter* species. Systematic and Applied Microbiology, 34, 171-179.

Zhang X, Liu X, Hu X, Tao K, Cao L, & Hu X. 2017. *Salix integra* combined with *Pseudomonas aeruginosa* to restore diesel contaminated soils. Journal of Environmental Engineering. 143, 04017037.

Zinniel, D. K., Lambrecht, P., Harris, N. B., Feng, Z., Kuczmarski, D., Higley, P., Ishimaru, C. A., Arunakumari, A., Barletta, R. G., and Vidaver, A. K. 2002. Isolation and characterization of endophytic colonizing bacteria from agronomic crops and prairie plants. Appl. Environ. Microbiol. 68(5):2198-2208.

TABLE 1

Siderophore assay of calcium phosphate solubilizing strains

| Strain | Growth | Siderophore production |
|---|---|---|
| KGS-1 | +++ | +++ |
| KGS-2 | +++ | +++ |
| KGS-3* | + | + |
| KGS-4 | +++ | +++ |
| KGS-5 | +++ | +++ |
| KGS-6 | +++ | +++ |
| KGS-7 | +++ | +++ |
| KGS-8 | +++ | +++ |
| KGS-9 | +++ | +++ |
| KGS-10 | +++ | +++ |

The plates were analyzed after incubating overnight except for KGS-3. The data for KGS-3 was obtained after 3 days of incubation

TABLE 2

SEED VIGOR INDEX OF TREATED (KGS-2) AND UNTREATED (CONTROL) SEEDS

| | SVI CONTROL | SVI 10 KGS-2 | % IMPROVEMENT[1] |
|---|---|---|---|
| Barley | 23563 | 29431 | 25 |
| Winter wheat | 49140 | 64240 | 31 |
| Spring wheat | 11819 | 18098 | 53 |
| Canola | 6363 | 7896 | 24 |
| Soybean | 2286 | 2921 | 28 |
| Corn | 4681 | 4200 | −10 |
| Fava | 20358 | 26240 | 29 |

TABLE 2-continued

SEED VIGOR INDEX OF TREATED (KGS-2) AND UNTREATED (CONTROL) SEEDS

| | SVI CONTROL | SVI 10 KGS-2 | % IMPROVEMENT[1] |
|---|---|---|---|
| Flax | 20790 | 22100 | 6 |
| Alfalfa | 10934 | 12308 | 13 |

[1]Highlighted number indicates statistically significant result at p-value of 0.05

TABLE 3

Plate count results from 1 gram of DE inoculated with $1.04 \times 10^8$ of KGS-2 cells

| Dilution | Replicate | Number of colonies | CFU/mL | CFU in 10 mL suspension |
|---|---|---|---|---|
| $10^3$ | 1 | TNTC | NA | NA |
| $10^3$ | 2 | TNTC | NA | NA |
| $10^3$ | 3 | TNTC | NA | NA |
| $10^4$ | 1 | 60 | $6.0 \times 10^6$ | $6.0 \times 10^7$ |
| $10^4$ | 2 | 49 | $4.9 \times 10^6$ | $4.9 \times 10^7$ |
| $10^4$ | 3 | 68 | $6.8 \times 10^6$ | $6.8 \times 10^7$ |

100 μL samples from each dilution was utilized for spread plating
CFU = Colony forming unit
TNTC = Too numerous to count,
NA = Not applicable
Only the count of 30-300 colonies in a single plate is considered significant and included in the data analysis CFU in 10 mL suspension=CFU/mL×10 mL This is because the dry inoculum was submerged in 10 mL of sterile water for this analysis Recovery percentage=CFU in 1 gram of DE/the original amount used to inoculate DE The data can be used to calculate the average and standard deviation The recovery percentage of bacteria from inoculum is 5.7±0.9%.

TABLE 4

Plate count results from 1 gram of DE inoculated with $1.04 \times 10^9$ of KGS-2 cells

| Dilution | Replicate | Number of colonies | CFU/mL | CFU in 10 mL suspension |
|---|---|---|---|---|
| $10^3$ | 1 | TNTC | NA | NA |
| $10^3$ | 2 | TNTC | NA | NA |
| $10^3$ | 3 | TNTC | NA | NA |
| $10^4$ | 1 | 54 | $5.4 \times 10^6$ | $5.4 \times 10^7$ |
| $10^4$ | 2 | 47 | $4.7 \times 10^6$ | $4.7 \times 10^7$ |
| $10^4$ | 3 | 46 | $4.6 \times 10^6$ | $4.6 \times 10^7$ |

100 μL samples from each dilution was utilized for spread plating
CFU = Colony forming unit
TNTC = Too numerous to count,
NA = Not applicable Only the count of 30-300 colonies in a single plate is considered significant and included in the data analysis CFU in 10 mL suspension=CFU/mL×10 mL This is because the dry inoculum was submerged in 10 mL of sterile water for this analysis Recovery percentage=CFU in 1 gram of DE/the original amount used to inoculate DE The data can be used to calculate the average and standard deviation The recovery percentages of bacteria from inoculum is 4.7±0.4%.

The invention claimed is:

1. A method for promoting or increasing or improving plant growth and/or plant yield comprising:
   preparing a composition comprising a high-density aliquot of plant growth promoting bacteria (PGPB) KGS-2 *Pseudomonas jessenii* strain deposited as IDAC:220318-01, said high-density aliquot comprising at least $1\times10^3$ colony forming units of PGPB KGS-2 per ml;
   applying said composition to a soil environment in which seeds or seedlings have been or will be planted;
   growing said seeds or seedlings into plants in said soil environment, said PGPB KGS-2 colonizing said soil environment and promoting growth of the plant; and harvesting said plants.

2. The method according to claim 1 wherein the soil environment includes phosphorus as a fertilizer.

3. The method according to claim 1 wherein the composition is applied to the soil environment as a coating on seeds.

4. The method according to claim 1 wherein the PGPB KGS-2 is applied to the soil environment as a liquid suspension.

5. The method according to claim 1 wherein the composition is applied as a liquid suspension on plants, on post emergent plants, on seeds, on seedlings, or on carrier materials.

6. The method according to claim 1 wherein the plants show increased growth compared to similar plants grown in an untreated soil environment.

7. The method according to claim 1 wherein PGPB KGS-2 increases or improves growth of plants by increasing root growth, increasing shoot growth, improving or increasing plant tolerance to stresses such as soil salinity, drought, and hydrocarbon and/or heavy-metal toxicity, increasing soil phosphate bioavailability, increasing plant size during early growth, inhibiting fungal infection of the plant or by establishing an endophytic relationship with the plants.

8. The method according to claim 1 wherein the PGPB KGS-2 improves or increases plant growth by converting glucose to gluconate, thereby lowering local soil pH and enhancing bioavailability of phosphate present in the soil environment.

9. The method according to claim 1 wherein the PGPB KGS-2 improves or increases plant growth by producing mannitol-2 dehydrogenase, thereby inhibiting fungal infections.

10. The method according to claim 1 wherein the PGPB KGS-2 improves or increases plant growth by synthesizing indole-3-acetic acid.

11. The method according to claim 1 wherein the PGPB KGS-2 improves or increases plant growth by degrading 1-aminocyclopropane-1-carboxylate.

12. The method according to claim 1 wherein the PGPB KGS-2 improves or increases plant growth by modulating levels of auxin.

13. The method according to claim 1 wherein the PGPB KGS-2 improves or increases growth by penetrating stems of a plant or embryo of a seed, thereby establishing an endophytic relationship.

14. A method for promoting or increasing or improving plant growth and/or plant yield comprising:
   preparing a composition comprising a high-density aliquot of plant growth promoting bacteria (PGPB) KGS-2 *Pseudomonas jessenii* strain deposited as IDAC:220318-01, said high-density aliquot comprising at least $1\times10^3$ colony forming units of PGPB KGS-2 per ml;
   applying said composition to seeds or seedlings that have been or will be planted in a soil environment, said KGS-2 penetrating said seeds or seedlings and establishing an endophytic relationship;
   growing said seeds or seedlings into plants in said soil environment; and harvesting said plants.

15. The method according to claim 14 wherein the composition is applied to seeds that will be planted.

* * * * *